United States Patent
Zhang et al.

(10) Patent No.: US 12,365,865 B2
(45) Date of Patent: Jul. 22, 2025

(54) SCALABLE CLARIFICATION PROCESS FOR RECOMBINANT AAV PRODUCTION

(71) Applicant: REGENXBIO INC., Rockville, MD (US)

(72) Inventors: Claire G. Zhang, Rockville, MD (US); Shaojie Weng, Rockville, MD (US); Ya-Chen Chang, Rockville, MD (US); Franz M. Gerner, Rockville, MD (US)

(73) Assignee: REGENXBIO INC., Rockville, MD (US)

( * ) Notice: Subject to any disclaimer, the term of this patent is extended or adjusted under 35 U.S.C. 154(b) by 215 days.

(21) Appl. No.: 17/050,608

(22) PCT Filed: Apr. 27, 2019

(86) PCT No.: PCT/US2019/029539
§ 371 (c)(1),
(2) Date: Oct. 26, 2020

(87) PCT Pub. No.: WO2019/212921
PCT Pub. Date: Nov. 7, 2019

(65) Prior Publication Data
US 2024/0254430 A1    Aug. 1, 2024

Related U.S. Application Data

(60) Provisional application No. 62/664,254, filed on Apr. 29, 2018, provisional application No. 62/671,968, filed on May 15, 2018.

(51) Int. Cl.
| | |
|---|---|
| *C12M 1/00* | (2006.01) |
| *B01D 39/18* | (2006.01) |
| *B01D 39/20* | (2006.01) |
| *C12N 15/86* | (2006.01) |

(52) U.S. Cl.
CPC ............ *C12M 47/02* (2013.01); *B01D 39/18* (2013.01); *B01D 39/2068* (2013.01); *C12N 15/86* (2013.01); *B01D 2239/065* (2013.01); *C12N 2750/14143* (2013.01); *C12N 2750/14151* (2013.01)

(58) Field of Classification Search
None
See application file for complete search history.

(56) References Cited

U.S. PATENT DOCUMENTS

| | | | |
|---|---|---|---|
| 6,566,118 B1 * | 5/2003 | Atkinson | C07D 207/32 435/235.1 |
| 11,021,689 B2 * | 6/2021 | Brument | C12Y 301/04035 |
| 11,203,740 B2 * | 12/2021 | Brument | B01D 69/02 |
| 2007/0172846 A1 * | 7/2007 | Zhang | C12N 15/86 435/5 |
| 2013/0012689 A1 * | 1/2013 | Singh | C02F 1/52 210/767 |
| 2016/0289633 A1 * | 10/2016 | Yang | C12N 5/0018 |
| 2020/0224173 A1 * | 7/2020 | Clement | C12N 7/00 |

FOREIGN PATENT DOCUMENTS

| | | | |
|---|---|---|---|
| EP | 3054007 | 8/2016 | |
| WO | 03/097797 | 11/2003 | |
| WO | 2010/148143 | 12/2010 | |
| WO | WO-2010148143 A1 * | 12/2010 | C07K 14/005 |
| WO | 2011/009613 | 1/2011 | |
| WO | WO-2017100676 A1 * | 6/2017 | B01D 15/3804 |
| WO | WO-2018226887 A1 * | 12/2018 | C12N 15/09 |

OTHER PUBLICATIONS

Tomic, S., Besnard, L., Fürst, B., Reithmeier, R., Wichmann, R., Schelling, P., & Hakemeyer, C. (2015). Complete clarification solution for processing high density cell culture harvests. Separation and Purification Technology, 141, 269-275. (Year: 2015).*
International Search Report and Written Opinion of the ISA for PCT/US2019/029539, mailed Aug. 13, 2019, 16 pages.
Felo et al., "Process cost and facility considerations in the selection of primary cell culture clarification technology", Biotechnology Progress, vol. 29, No. 5, Jul. 11, 2013, pp. 1239-1245.
"Clarification of mammaliancell cultures by depth filtration", Millipore Filtration, Separation & Preparation, Mar. 1, 2017, XP002792835, 2 pages.
Besnard et al., "Clarification of vaccines: An overview of filter based technology trends and best practices", Biotechnology Advances, vol. 34, No. 1, Dec. 2, 2015, pp. 1-13.
Prashad et al., "Depth filtration: Cell clarification of bioreactor offloads", Filtration and Separation, vol. 43, No. 7, Sep. 1, 2006, pp. 28-30.
Weng, "Development of a scalable AAV harvest clarification process", Molecular Therapy, vol. 26, No. 5, May 1, 2018, 1 page.

* cited by examiner

*Primary Examiner* — Janet L Andres
*Assistant Examiner* — Carey Alexander Stuart
(74) *Attorney, Agent, or Firm* — NIXON & VANDERHYE, PC

(57) ABSTRACT

Provided herein are scalable methods for the clarification of a composition comprising recombinant Adeno-Associated Virus (rAAV) particles and an impurity.

17 Claims, 3 Drawing Sheets

Specification includes a Sequence Listing.

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: AAV capsid polypeptide insertion sequence

<400> SEQUENCE: 1

Leu Gly Glu Thr Thr Arg Pro
1               5

<210> SEQ ID NO 2
<211> LENGTH: 9
<212> TYPE: PRT
<213> ORGANISM: Artificial Sequence
<220> FEATURE:
<223> OTHER INFORMATION: AAV capsid polypeptide insertion sequence

<400> SEQUENCE: 2

Leu Ala Leu Gly Glu Thr Thr Arg Pro
1               5
```

SCALABLE CLARIFICATION PROCESS FOR RECOMBINANT AAV PRODUCTION

CROSS-REFERENCE TO RELATED APPLICATIONS

This application is the U.S. national phase of International Application No. PCT/US2019/029539 filed 27 Apr. 2019, which designated the U.S. and claims the benefit of priority of U.S. Provisional Application Nos. 62/664,254 filed Apr. 29, 2018, and 62/671,968 filed May 15, 2018, the entire content of each of which is incorporated herein in its entirety.

REFERENCE TO SEQUENCE LISTING SUBMITTED ELECTRONICALLY

The content of the electronically submitted sequence listing (Name: 6728.0110_Sequence_Listing.txt; Size: 797 bytes; and Date of Creation: Jul. 19, 2021) filed on Jul. 22, 2021 is incorporated herein by reference in its entirety.

BACKGROUND

Recombinant Adeno-Associated Virus (AAV)-based vectors are currently the most widely used gene therapy products in development. The preferred use of rAAV vector systems is due, in part, to the lack of disease associated with the wild-type virus, the ability of AAV to transduce non-dividing as well as dividing cells, and the resulting long-term robust transgene expression observed in clinical trials and that indicate great potential for delivery in gene therapy indications. Additionally, different naturally occurring and recombinant rAAV vector serotypes, specifically target different tissues, organs, and cells, and help evade any pre-existing immunity to the vector, thus expanding the therapeutic applications of AAV-based gene therapies.

However, before AAV based gene therapies can be more widely adopted for late clinical stage and commercial use, new methods for large scale GMP compliant purification of rAAV particles need to be developed. Most rAAV purification strategies employ only inert filters (such as polypropylene (PP), polyvinylidene fluoride (PVDF), or polyethersulfone (PES)) because AAV is known to bind to many types of filter membranes, resulting in significant product loss. Inert filters, however, are inappropriate for removing cells and cell debris to clarify a cell culture feed because of their low capacity. Instead, rAAV producing cell culture clarification is performed by centrifugation, which is time consuming and requires costly and complicated equipment. Thus, there is a need for scalable GMP compliant processes to clarify rAAV producing cell cultures using alternative clarification strategies.

BRIEF SUMMARY

The disclosure provides methods for clarifying a composition (e.g., a feed such as a cell culture or cell lysate) containing recombinant AAV (rAAV) particles and an impurity (e.g., cells or cellular debris) by subjecting the composition to multi-stage filtration, wherein the method clarifies the composition without the use of centrifugation or tangential flow microfiltration. In some embodiments, the methods include upstream processing (such as, for example, treatment with nuclease or endonuclease, addition of salt, pH adjustment, and/or addition of a flocculent, or any combination(s) thereof. In some embodiments, the methods include downstream processing (such as, for example, tangential flow filtration, affinity chromatography, anion exchange chromatography, hydrophobic interaction chromatography, size exclusion chromatography, and/or sterile filtration, or any combination(s) thereof. In further embodiments, the methods include upstream processing and downstream processing. The upstream and/or downstream processing may be used alone or in various combinations.

In additional embodiments, the disclosure provides methods for producing isolated recombinant adeno-associated virus (rAAV) particles from a composition (e.g., a feed such as cell culture or cell lysate) comprising recombinant AAV particles and an impurity (e.g., cells or cellular debris) by clarifying the composition using multi-stage filtration without the use of centrifugation or tangential flow microfiltration, and isolating the rAAV particles from the clarified composition by one or more of tangential flow filtration, affinity chromatography, size exclusion chromatography, ion exchange chromatography, and hydrophobic interaction chromatography. In some embodiments, the methods include upstream processing of the composition, including for example, treatment with nuclease (e.g., Benzonase®) or endonuclease (e.g., endonuclease from *Serratia marcescens*), addition of salt, pH adjustment, and/or addition of a flocculent, or any combination(s) thereof.

In some embodiments, the disclosure provides:

[1] a method for the clarification of a feed containing recombinant adeno-associated virus (rAAV) particles and an impurity comprising:
  (a) contacting the feed with a primary depth filter to generate a primary filtrate comprising the rAAV particles;
  (b) contacting the primary filtrate with a secondary depth filter to generate a secondary filtrate comprising the rAAV particles; and
  (c) recovering the secondary filtrate; wherein
  (i) the feed comprises a cell culture, a cell lysate, or a combination thereof,
  (ii) the impurity comprises cells or cellular debris, and
  (iii) the method separates the rAAV particles from the impurity without the use of centrifugation or tangential flow microfiltration prior to (a);

[2] the method of [1], wherein the primary filtrate is directly loaded to the secondary depth filter;

[3] the method of [1] or [2], which further comprises:
  (d) contacting the secondary filtrate with a tertiary filter to generate a tertiary filtrate comprising the rAAV particles; and
  (e) recovering the tertiary filtrate;

[4] the method of [3], wherein the secondary filtrate is directly loaded to the tertiary filter;

[5] the method of any one of [1] to [4], wherein the primary depth filter comprises a porous depth filter media comprising at least 2 graded layers of non-woven fibers having a total thickness of about 0.3 cm to about 3 cm, and wherein each of the at least 2 graded layers of non-woven fibers have a nominal pore size rating more than about 40 µm;

[6] the method of [5], wherein the porous depth filter media is anisotropic;

[7] the method of [5] or [6], wherein the porous depth filter media comprises at least 3 graded layers of non-woven fibers;

[8] the method of any one of [5] to [7], wherein the porous depth filter media comprises a composite of graded layers of non-woven fibers, cellulose, and diatomaceous earth;

[9] the method of any one of [5] to [8], wherein the non-woven fibers comprise polypropylene, polyethylene, polyester, nylon, or a combination thereof;

[10a] the method of any one of [5] to [9], wherein the porous depth filter media [10a] has an open nominal pore size rating between about 60 μm and about 0.5 μm;

[10b] the method of any one of [5] to [9], wherein the porous depth filter media [10b] has an open nominal pore size rating between about 50 μm and about 0.5 μm;

[10c] the method of any one of [5] to [9], wherein the porous depth filter media has an open nominal pore size rating between about 40 μm and about 0.5 μm;

[11] the method of any one of [5] to [9], wherein the porous depth filter media has an open nominal pore size rating between about 30 μm and about 0.5 μm;

[12] the method of any one of [5] to [9], wherein the porous depth filter media has an open nominal pore size rating between about 25 μm and about 0.5 μm;

[13] the method of any one of [5] to [9], wherein the porous depth filter media has an open nominal pore size rating between about 20 μm and about 0.5 μm;

[14] the method of any one of [5] to [9], wherein the porous depth filter media has an open nominal pore size rating between about 18 μm and about 0.6 μm;

[15] the method of any one of [5] to [14], wherein the porous depth filter media is Clarisolve® 20 MS;

[16] the method of any one of [1] to [15], wherein the secondary depth filter comprises a media comprising a composite of cellulose and diatomaceous earth;

[17] the method of [16], wherein the secondary depth filter comprises a media comprising a first layer of a composite of cellulose and diatomaceous earth and a second layer of a composite of cellulose and diatomaceous earth;

[18] the method of [17], wherein the first layer has an open nominal pore size rating between about 5 μm and about 0.5 μm and the second layer has an open nominal pore size rating between about 0.8 μm and about 0.1 μm;

[19] the method of [18], wherein the first layer has an open nominal pore size rating between about 2 μm and about 0.5 μm and the second layer has an open nominal pore size rating between about 0.5 μm and about 0.1 μm;

[20] the method of [18], wherein the first layer has an open nominal pore size rating of about 1.2 μm and the second layer has an open nominal pore size rating of about 0.2 μm;

[21] the method of any one of [17] to [18], wherein the secondary depth filter comprises a media having an open nominal pore size rating between about 5 μm and about 0.1 μm;

[22] the method of [21], wherein the secondary depth filter comprises a media having an open nominal pore size rating between about 2 μm and about 0.1 μm;

[23] the method of [22], wherein the secondary depth filter comprises a media having an open nominal pore size rating between about 1.2 μm and about 0.2 μm;

[24] the method of any one of [1] to [23], wherein the secondary depth filter comprises Millistak+® COHC;

[25] the method of any one of [3] to [24], wherein the tertiary filter comprises a sterilizing grade filter media;

[26] the method of any one of [3] to [25], wherein the tertiary filter comprises polyethersulfone;

[27] the method of any one of [3] to [26], wherein the tertiary filter comprises a media comprising a hydrophilic heterogeneous double layer design;

[28] the method of any one of [3] to [27], wherein the tertiary filter comprises media comprising a hydrophilic heterogeneous double layer design of a 0.8 μm pre-filter and 0.2 μm final filter membrane;

[29a] the method of any one of [3] to [28], wherein the tertiary filter comprises Sartopore® 2 XLG 0.2 μm;

[29b] the method of any one of [3] to [28], wherein the tertiary filter comprises a filter with a pore size between about 0.2 μm and about 0.1 μm;

[29c] the method of any one of [3] to [28], wherein the tertiary filter comprises a filter with a pore size of about 0.1 μm;

[30] the method of any one of [1] to [29], wherein the ratio of primary filter area to secondary filter area is between about 1:3 and about 3:1;

[31] the method of [30], wherein the ratio of primary filter area to secondary filter area is between about 1:2 and about 2:1;

[32] the method of [30], wherein the ratio of primary filter area to secondary filter area is about 1:1;

[33] the method of any one of [1] to [32], wherein the ratio of primary filter area to tertiary filter area is between about 1:3 and about 3:1;

[34] the method of [33], wherein the ratio of primary filter area to tertiary filter area ratio is about 1:1;

[35] the method of any one of [1] to [34], wherein the ratio of primary filter area to secondary filter area to tertiary filter area ratio is within the range of about 0.3-3 to about 0.3-3 to about 0.2-5;

[36] the method of [35], wherein the ratio of primary filter area to secondary filter area to tertiary filter area ratio is (a) about 2 to about 1 to about 1, (b) about 1 to about 1 to about 1, or about 8 to about 5 to about 4;

[36a] the method of any one of [1] to [36], wherein the primary filter has a capacity of between about 50 $L/m^2$ and about 400 $L/m^2$ at 200 LMH;

[36b] the method of [36a], wherein the primary filter has a capacity of between about 200 $L/m^2$ and about 400 $L/m^2$ at 200 LMH;

[36c] the method of [36a], wherein the primary filter has a capacity of higher than about 225 $L/m^2$ at 200 LMH;

[36d] the method of any one of [36a] to [36c], wherein the capacity of the primary filter has been determined using a constant flow method, wherein the feed comprises a cell culture, wherein more than about 60% of the cells in the culture are viable;

[36e] the method of any one of [1] to [36d], wherein the secondary filter has a capacity of between about 250 $L/m^2$ and about 650 $L/m^2$ at 200 LMH;

[36f] the method of [36e], wherein the secondary filter has a capacity of more than about 450 $L/m^2$ at 200 LMH;

[36g] the method of [36e] or [36f], wherein the capacity of the secondary filter has been determined using a constant flow method, wherein the feed comprises the primary filtrate;

[36h] the method of any one of [1] to [36g], wherein the tertiary filter has a capacity of between about 400 $l/m^2$ and about 2500 $L/m^2$ at 200 LMH;

[36i] the method of [36h], wherein the tertiary filter has a capacity of more than about 450 $L/m^2$ at 200 LMH;

[36j] the method of [36h] or [36i], wherein the capacity of the tertiary filter has been determined using a constant flow method, wherein the feed comprises the secondary filtrate;

[37] the method of any one of [1] to [36j], wherein the feed comprises a cell culture and the cell culture is a suspension culture;

[38] the method of [37], wherein the suspension culture comprises a culture of HeLa cells, HEK293 cells, or SF-9 cells;

[39] the method of [37], wherein the suspension culture comprises a culture of HEK293 cells;

[40] the method of any one of [37] to [39], wherein the culture has a total cell density of between about 1×10E+06 cells/ml and about 30×10E+06 cells/ml;

[41] the method of [40], wherein the culture has a total cell density of between about 5×10E+06 cells/ml and about 25×10E+06 cells/ml;

[42] the method of [41], wherein the culture has a total cell density of between about 10×10E+06 cells/ml and about 20×10E+06 cells/ml;

[43] the method of any one of [37] to [42], wherein between about 40% and about 90% of the cells are viable cells;

[44] the method of [43], wherein between about 60% and about 80% of the cells are viable cells;

[45] the method of any one of [37] to [42], wherein more than about 50% of the cells are viable cells;

[46] the method of [45], wherein more than about 60% of the cells are viable cells;

[47] the method of [46], wherein more than about 70% of the cells are viable cells;

[48] the method of any one of [37] to [47], further comprising pretreating the feed before contacting the feed with the primary depth filter;

[49] the method of [48], wherein the pretreating comprises adding salt to the feed;

[50] the method of [49], wherein the pretreating comprises adding salt to the feed to a final concentration between about 0.2 M and about 0.6 M;

[51] the method of [50], wherein the pretreating comprises adding salt to a final concentration of about 0.3 M;

[52] the method of [50], wherein the pretreating comprises adding salt to a final concentration of about 0.5 M;

[53] the method of any one of [49] to [52], wherein the salt is NaCl;

[54] the method of any one of [37] to [47], wherein the feed is not pre-treated before contacting the feed with the primary depth filter;

[55] the method of any one of [1] to [54], wherein the method is performed at a flux of about 50 LMH;

[56] the method of any one of [1] to [54], wherein the method is performed at a flux between about 150 LMH and about 250 LMH;

[57] the method of [56], wherein the method is performed at a flux between about 175 LMH and about 225 LMH;

[58] the method of [56], wherein the method is performed at a flux between about 190 LMH and about 210 LMH;

[59] the method of [56], wherein the method is performed at a flux of about 225 LMH;

[60] the method of [56], wherein the method is performed at a flux of about 200 LMH;

[61] the method of any one of [1] to [60], wherein the turbidity of the secondary filtrate is less than about 50 NTU;

[62] the method of [61], wherein the turbidity of the secondary filtrate is less than about 25 NTU;

[63] the method of [62], wherein the turbidity of the secondary filtrate is less than about 10 NTU;

[64] the method of [63], wherein the turbidity of the secondary filtrate is less than about 5 NTU;

[65] the method of [64], wherein the turbidity of the secondary filtrate is less than about 3 NTU;

[66] the method of [65], wherein the turbidity of the secondary filtrate is less than about 2 NTU;

[67] the method of any one of [3] to [66], wherein the turbidity of the tertiary filtrate is less than about 50 NTU;

[68] the method of [67], wherein the turbidity of the tertiary filtrate is less than about 25 NTU;

[69] the method of [68], wherein the turbidity of the tertiary filtrate is less than about 10 NTU;

[70] the method of [69], wherein the turbidity of the tertiary filtrate is less than about 5 NTU;

[71] the method of [70], wherein the turbidity of the tertiary filtrate is less than about 3 NTU;

[72] the method of [71], wherein the turbidity of the tertiary filtrate is less than about 2 NTU;

[73] the method of any one of [1] to [72], wherein the yield of rAAV particles in the secondary or tertiary filtrate is at least about 50%;

[74] the method of [72], wherein the yield of rAAV particles in the secondary or tertiary filtrate is at least about 60%;

[75] the method of [72], wherein the yield of rAAV particles in the secondary or tertiary filtrate is at least about 70%;

[76] the method of [72], wherein the yield of rAAV particles in the secondary or tertiary filtrate is at least about 80%;

[77] the method of [72], wherein the yield of rAAV particles in the secondary or tertiary filtrate is at least about 90%;

[78a] the method of [72], wherein the yield of rAAV particles in the secondary filtrate is at least about 95%;

[78b] the method of [72], wherein the yield of rAAV particles in the tertiary filtrate is at least about 95%;

[78c] the method of [72], wherein the yield of rAAV particles in the secondary filtrate is at least about 96%;

[78d] the method of [72], wherein the yield of rAAV particles in the tertiary filtrate is at least about 96%;

[78e] the method of [72], wherein the yield of rAAV particles in the secondary filtrate is at least about 97%;

[78fb] the method of [72], wherein the yield of rAAV particles in the tertiary filtrate is at least about 97%;

[78g] the method of [72], wherein the yield of rAAV particles in the secondary filtrate is at least about 98%;

[78h] the method of [72], wherein the yield of rAAV particles in the tertiary filtrate is at least about 98%;

[78i] the method of [72], wherein the yield of rAAV particles in the secondary filtrate is at least about 99%;

[78j] the method of [72], wherein the yield of rAAV particles in the tertiary filtrate is at least about 99%;

[79] the method of any one of [1] to [78j], wherein the rAAV particles comprise an AAV capsid protein from an AAV selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16;

[80] the method of [79], wherein the AAV capsid serotype is AAV-8;

[81] the method of [79], wherein the AAV capsid serotype is AAV-9;
[82] the method of any one of claims 1 to 81, wherein the feed volume is between about 50 liters and about 20,000 liters;
[83] the method of [82], wherein the feed volume is between about 100 liters and about 3000 liters;
[84] the method of [82], wherein the feed volume is between about 500 liters and about 3000 liters;
[85] the method of [82], wherein the feed volume is between about 1500 liters and about 2500 liters;
[86] the method of [82], wherein the feed volume is about 2000 liters;
[87] the method of [82], wherein the feed volume is about 1000 liters;
[88] a method for producing a composition comprising isolated recombinant adeno-associated virus (rAAV) particles from a feed comprising an impurity, comprising:
  (a) clarifying the feed according to the method of any one of claims 1 to 81, and
  (b) isolating the rAAV particles from the clarified feed by one or more of tangential flow filtration, affinity chromatography, size exclusion chromatography, ion exchange chromatography, and hydrophobic interaction chromatography;
[89] the method of [88], wherein the isolating the rAAV particles comprises a tangential flow filtration;
[90] the method of [88], wherein the isolating the rAAV particles comprises a first tangential flow filtration, affinity chromatography, anion exchange chromatography, and a second tangential flow filtration;
[91] the method of [90], wherein the isolating the rAAV particles further comprises a sterile filtration;
[92] the method of any one of [88] to [91], further comprising determining the vector genome titer of the composition comprising the isolated recombinant rAAV particles comprising:
  (a) measuring the absorbance of the composition at 260 nm; and
  (b) measuring the absorbance of the composition at 280 nm;
[93] the method of any one of [88] to [91], further comprising determining the capsid titer of the composition comprising the isolated recombinant rAAV particles comprising:
  (a) measuring the absorbance of the composition at 260 nm; and
  (b) measuring the absorbance of the composition at 280 nm;
[94] the method of [93] or [94], the rAAV particles are not denatured prior to measuring the absorbance of the composition;
[95] the method of [93] or [94], the rAAV particles are denatured prior to measuring the absorbance of the composition;
[96] the method of any one of [91] to [95], wherein the absorbance of the composition at 260 nm and 280 nm is determined using a spectrophotometer;
[97] the method of any one of [91] to [95], wherein the absorbance of the composition at 260 nm and 280 nm is determined using a HPLC;
[98] the method of [97], wherein the absorbance is peak absorbance;
[99] a composition comprising isolated recombinant rAAV particles produced by a method of any one of [88] to [99]; or
[100] the composition of [99] which is a pharmaceutical composition.

In some embodiments, [1](a)-[1](b) is in fluid communication. The term "fluid communication," refers to the flow of fluid material between two process steps or flow of fluid material between steps of a process step, wherein the process steps are connected by any suitable means (e.g., a connecting line or surge tank), thereby to enable the flow of fluid from one process step to another process step. In some embodiments according to the disclosed methods, the primary depth filter is in fluid communication with the secondary depth filter. In some embodiments, a connecting line between the primary depth filter and the secondary depth filter may be interrupted by one or more valves to control the flow of fluid through the connecting line.

In some embodiments, one or both of [1](a)-[1](b) or [1](b)-[1](c) involve a continuous process. A "continuous process" refers to a method which includes two or more process steps, such that the output from one process step flows directly into the next process step in the process, without interruption, and where two or more process steps can be performed concurrently for at least a portion of their duration. In other words, in case of a continuous process, as described herein, it is not necessary to complete a process step before the next process step is started, but a portion of the sample is always moving through the process steps. In some embodiments, the method of (a) contacting the feed with a primary depth filter to generate a primary filtrate comprising the rAAV particles; and (b) contacting the primary filtrate with a secondary depth filter to generate a secondary filtrate comprising the rAAV particles is a continuous process. In some embodiments, the method of (b) contacting the primary filtrate with a secondary depth filter to generate a secondary filtrate comprising the rAAV particles and (c) recovering the secondary filtrate is a continuous process. In some embodiments, the method of (a) contacting the feed with a primary depth filter to generate a primary filtrate comprising the rAAV particles; and (b) contacting the primary filtrate with a secondary depth filter to generate a secondary filtrate comprising the rAAV particles is a continuous process. In some embodiments, the method of (a) contacting the feed with a primary depth filter to generate a primary filtrate comprising the rAAV particles; (b) contacting the primary filtrate with a secondary depth filter to generate a secondary filtrate comprising the rAAV particles; and (c) recovering the secondary filtrate is a continuous process.

In some embodiments, the methods include upstream processing to prepare the feed containing rAAV particles used according to the method of any one of [1] to [91]. In further embodiments, the upstream processing is at least one of addition of nuclease or endonuclease (e.g., endonuclease from *Serratia marcescens*), addition of salt, pH adjustment, or addition of a flocculent. In further embodiments, the upstream processing includes at least 2, at least 3, or at least 4 of: addition of nuclease (e.g., Benzonase®) or endonuclease (e.g., endonuclease from *Serratia marcescens*), addition of salt, pH adjustment, and/or addition of a flocculent. In some embodiments, the upstream processing does not include centrifugation of the composition (feed). In some embodiments, the upstream processing does not include tangential flow microfiltration of the composition (feed). In further embodiments, the upstream processing does not include centrifugation or tangential flow microfiltration of the composition (feed).

In additional embodiments, the methods include further downstream processing (i.e., after the production of clarified feed according to the disclosed methods) of the rAAV containing composition recovered according to the method of any one of [1] to [91]. In some embodiments, the further downstream processing includes at least one of tangential flow filtration, affinity chromatography, anion exchange chromatography, hydrophobic interaction chromatography, size exclusion chromatography, or sterile filtration. In some embodiments, the further downstream processing includes at least 2, at least 3, or at least 4 of: tangential flow filtration, affinity chromatography, anion exchange chromatography, hydrophobic interaction chromatography, size exclusion chromatography, or sterile filtration. In some embodiments, the further downstream processing includes tangential flow filtration. In some embodiments, the further downstream processing includes sterile filtration. In further embodiments, the further downstream processing includes tangential flow filtration and sterile filtration.

DETAILED DESCRIPTION

Figure 1:
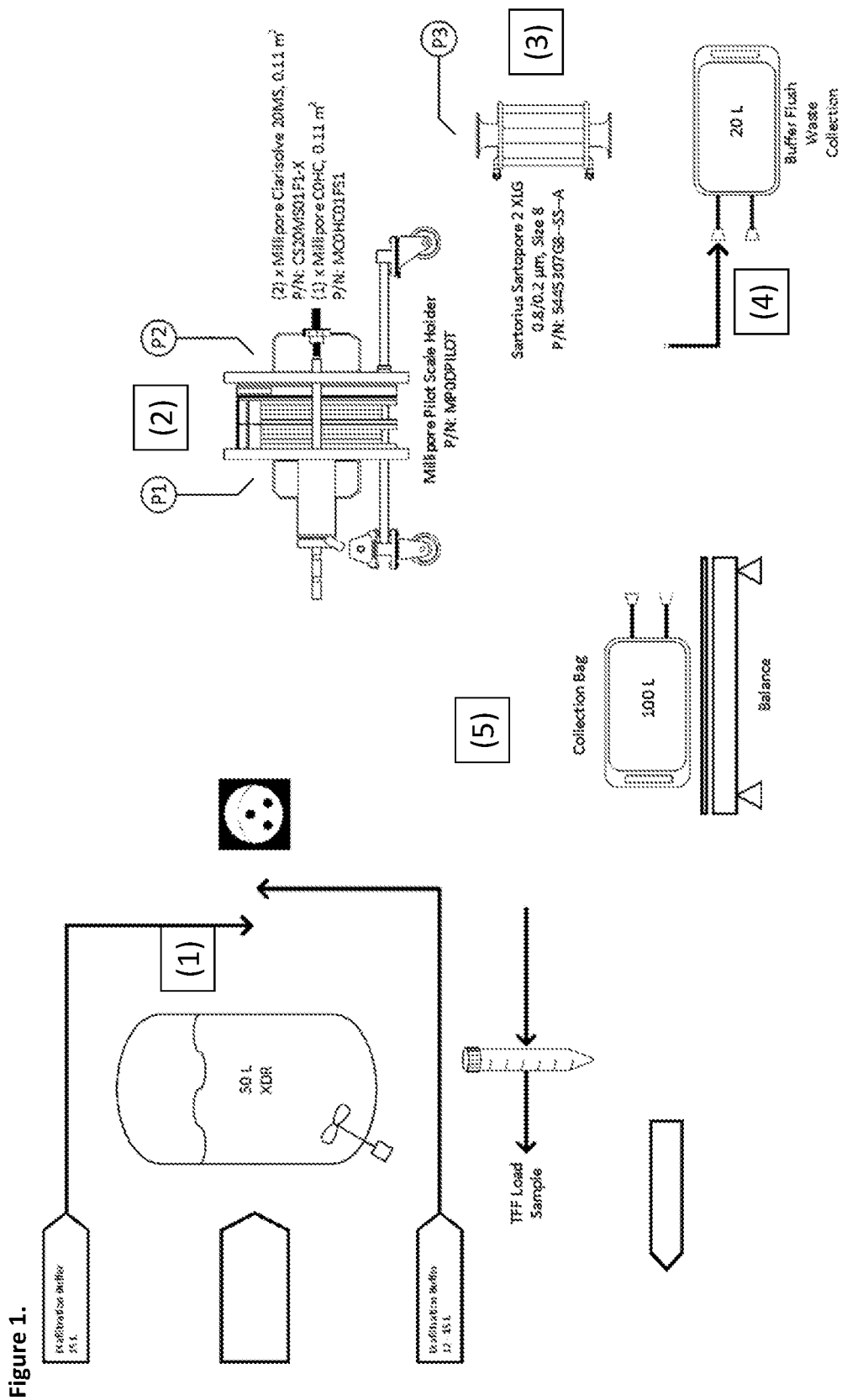
FIG. 1 is a schematic outline of a suspension culture clarification process using a filter train of Clarisolve® 20 MS, Millistak+® COHC, and Sartopore® 2 XLG 0.2 µm filters. (1) Suspension cell culture was directly loaded on the filter train. (2) Filtration system set-up on the Millipore Pilot Scale Pod Holder: Clarisolve 20 MS and COHC were set up on the Pod Holder, separated by a Millipore POD flow diverter, to remove whole cells, cell debris, fines and some aggregates. (3) Sterile filter Sartopore 2 XLG; (4) Buffer flush (20 mM Tris, 200 mM NaCl, pH7.5) went to waste bag. (5) Filtrate was collected in 100 L bag and followed by TFF step.

In some embodiments, the disclosure provides methods for clarifying a composition, for example, a high titer rAAV production culture harvest or feed by multi-stage filtration, wherein the method clarifies the composition without the use of centrifugation or tangential flow microfiltration, and the clarified composition is suitable for further downstream processing, for example, by tangential flow filtration, affinity chromatography, anion exchange chromatography, and sterile filtration, to produce isolated rAAV particles. The described methods provide flexible, cost-effective, single-use, commercially scalable processes consistent with GMP regulatory requirements for isolation of a population of rAAV particles for use in gene therapy applications. The methods described herein are suited to virtually any AAV serotype, including without limitation AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16, and derivatives, modifications, or pseudotypes thereof. In some embodiments, the methods are used to clarify compositions containing rAAV-8 particles. In some embodiments, the methods are used to clarify compositions containing rAAV-8 derivative particles, rAAV-8 modification particles, or rAAV-8 pseudotype particles. In some embodiments, the methods are used to clarify compositions containing rAAV-9 particles. In some embodiments, the methods are used to clarify compositions containing rAAV-9 derivative particles, rAAV-9 modification particles, or rAAV-9 pseudotype particles.

Definitions

Unless defined otherwise, all technical and scientific terms used herein have the same meaning as commonly understood by one of ordinary skill in the art to which this disclosure is related. To facilitate an understanding of the disclosed methods, a number of terms and phrases are defined below.

"About" modifying, for example, the quantity of an ingredient in the compositions, concentration of an filter surface area ratios, flux through filters, turbidity, rAAV particle yield, viable cell density, total cell viability, feed volume, salt concentration, and like values, and ranges thereof, employed in the methods provided herein, refers to variation in the numerical quantity that can occur, for example, through typical measuring and handling procedures used for making concentrates or use solutions; through inadvertent error in these procedures; through differences in the manufacture, source, or purity of the ingredients employed to make the compositions or carry out the methods; and like considerations. The term "about" also encompasses amounts that differ due to aging of a composition with a particular initial concentration or mixture. The term "about" also encompasses amounts that differ due to mixing or processing a composition with a particular initial concentration or mixture. Whether or not modified by the term "about" the claims include equivalents to the quantities. In some embodiments, the term "about" refers to ranges of approximately 10-20% greater than or less than the indicated number or range. In further embodiments, "about" refers to plus or minus 10% of the indicated number or range. For example, "about 10%" indicates a range of 9% to 11%.

"AAV" is an abbreviation for adeno-associated virus, and may be used to refer to the virus itself or modifications, derivatives, or pseudotypes thereof. The term covers all subtypes and both naturally occurring and recombinant forms, except where required otherwise. The abbreviation "rAAV" refers to recombinant adeno-associated virus. The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, and ovine AAV, and modifications, derivatives, or pseudotypes thereof. "Primate AAV" refers to AAV that infect primates, "non-primate AAV" refers to AAV that infect non-primate mammals, "bovine AAV" refers to AAV that infect bovine mammals, etc.

"Recombinant", as applied to a an AAV particle means that the AAV particle is the product of one or more procedures that result in an AAV particle construct that is distinct from an AAV particle in nature.

A recombinant Adeno-associated virus particle "rAAV particle" refers to a viral particle composed of at least one AAV capsid protein and an encapsidated polynucleotide rAAV vector comprising a heterologous polynucleotide (i.e. a polynucleotide other than a wild-type AAV genome such as a transgene to be delivered to a mammalian cell). The rAAV particle may be of any AAV serotype, including any modification, derivative or pseudotype (e.g., AAV-1, AAV-2, AAV-3, AAV-4, AAV-5, AAV-6, AAV-7, AAV-8, AAV-9, or AAV-10, or derivatives/modifications/pseudotypes thereof). Such AAV serotypes and derivatives/modifications/pseudotypes, and methods of producing such serotypes/derivatives/modifications/pseudotypes are known in the art (see, e.g., Asokan et al., Mol. Ther. 20(4):699-708 (2012).

The rAAV particles of the disclosure may be of any serotype, or any combination of serotypes, (e.g., a population of rAAV particles that comprises two or more serotypes, e.g., comprising two or more of rAAV2, rAAV8, and rAAV9 particles). In some embodiments, the rAAV particles are rAAV1, rAAV2, rAAV3, rAAV4, rAAV5, rAAV6, rAAV7, rAAV8, rAAV9, rAAV10, or other rAAV particles, or combinations of two or more thereof). In some embodiments, the rAAV particles are rAAV2, rAAV8 or rAAV9 particles.

In some embodiments, the rAAV particles have an AAV capsid protein of a serotype selected from the group consisting of AAV-1, AAV-2, AAV-3, AAV-4, AAV-5, AAV-6, AAV-7, AAV-8, AAV-9, AAV-10, AAV-11, AAV-12, AAV-13, AAV-14, AAV-15 and AAV-16 or a derivative, modification, or pseudotype thereof. In some embodiments, the rAAV particles have an AAV capsid protein of a serotype selected from the group consisting of AAV-1, AAV-4, AAV-5, and AAV-8 or a derivative, modification, or pseudotype thereof. In some embodiments, the rAAV particles have an AAV-8 or AAV-9 capsid serotype or a derivative, modification, or pseudotype thereof.

The term "impurity" or "contaminant" refers to any foreign or objectionable molecule, including a biological macromolecule such as DNA, RNA, one or more host cell proteins, endotoxins, lipids and one or more additives which may be present in a sample containing the rAAV particles that are being separated from one or more of the foreign or objectionable molecules using a disclosed method. Additionally, such impurity may include any reagent which is used in a step which may occur prior to one or more of the disclosed methods. An impurity may be soluble or insoluble in nature. Insoluble impurities include any undesirable or objectionable entity present in a sample containing rAAV particles, where the entity is a suspended particle or a solid. Exemplary insoluble impurities include without limitation, whole cells, cell fragments and cell debris. Soluble impurities include any undesirable or objectionable entity present in a sample containing rAAV particles where the entity is not an insoluble impurity. Exemplary soluble impurities include without limitation, host cell proteins, DNA, RNA, lipids viruses, endotoxins, and cell culture media components.

The term "cell culture," refers to cells grown in suspension, roller bottles, flasks and the like, as well as the components of the suspension itself, including but not limited to rAAV particles, cells, cell debris, cellular contaminants, colloidal particles, biomolecules, host cell proteins, nucleic acids, and lipids, and flocculants. Large scale approaches, such as bioreactors, including suspension cultures and adherent cells growing attached to microcarriers in stirred fermenters, are also encompassed by the term "cell culture." Cell culture procedures for both large and small-scale production of proteins are encompassed by the present disclosure.

The term "cell density" means the concentration of cells in a solution such as a cell culture or cell lysate (e.g., cells/mL). "Total cell density" refers to the total number of viable and non-viable cells in a solution. Cell density and total cell density can routinely be determined using techniques known in the art, such as by Trypan Blue exclusion using a Cedex Cell Counter and Analyzer (Roche Innovatis AG, Indianapolis, Ind.). Cell density may also be measured using for example, cytometry, packed cell volume determination, or Coulter counters (with the Electrical Sensing Zone Method). The term "viable cell density" refers to the number of living cells per unit volume. The term "% viability" means the percentage of live host cells in a solution.

The terms "lysate" or "cell lysate" refer to a composition primarily consisting of cells that have ruptured cell walls and/or cell membranes. Lysates may or may not have been fractionated to remove one or more cellular components.

The term "clarified liquid culture medium", or "clarified feed" is used herein to refer to a liquid culture medium obtained from a mammalian, bacterial, or yeast cell culture that is substantially free (such as at least 90%, 92%, 94%, 96%, 98%, or 99% free) of mammalian, bacterial, or yeast cells.

The term "feed" refers to a source of rAAV particles that is loaded onto, passed through, or applied to a filter or chromatographic matrix. Feeds encompassed by the disclosure include production culture harvests, and materials isolated from previous chromatographic steps encompassed by the disclosed methods whether the material was present as flow-through from the previous step, bound and eluted in the previous step, present in the void volume of the previous step or present in any fraction obtained during the purification of rAAV particles. Such feeds may include one or more contaminants. In some embodiments, the feed containing rAAV particles further comprises production culture contaminants such as damaged rAAV particles, host cell contaminants, helper virus contaminants, and/or cell culture contaminants. In some embodiments, the host cell contaminants comprise host cell DNA, plasmids, or host cell protein. In additional embodiments, the helper virus contaminants comprise adenovirus particles, adenovirus DNA, or adenovirus proteins. In some embodiments, the cell culture contaminants comprise media components, serum albumin, or other serum proteins. In additional embodiments, the cell culture contaminants comprise media components.

The term "filtrate" or "throughput" is a term of art and means a fluid that is emitted from a filter (e.g., a depth filter, a pre-filter, or a virus filter) that includes a detectable amount of a rAAV.

The terms "purifying", "purification", "separate", "separating", "separation", "isolate", "isolating", or "isolation", as used herein, refer to increasing the degree of purity of rAAV particles from a sample comprising the target molecule and one or more impurities. Typically, the degree of purity of the target molecule is increased by removing (completely or partially) at least one impurity from the sample. In some embodiments, the degree of purity of the rAAV in a sample is increased by removing (completely or partially) one or more impurities from the sample by using a method described herein.

The term "depth filter" is a term of art and means a filter that includes a porous filtration media that captures contaminants and/or impurities within its 3-dimensional structure and not merely on the surface. Depth filter clarification media are typically constructed from materials of a fibrous bed of cellulose, a wet-strength resin binder and an inorganic filter aid such as diatomaceous earth. The resin binder helps to impart wet tensile strength, provide an adsorptive charge to bind impurities and minimize shedding of the filter components. The diatomaceous earth provides a high surface area to the filter and contributes to the adsorptive properties. Depth filter media, unlike absolute filters, retain particles throughout the filter media. Depth filters are characterized in that they retain the contaminants or impurities within the filter and can retain a relatively large quantity before becoming clogged. Depth filter construction may include multiple layers, multiple membranes, a single layer, or a resin material. Non-limiting examples of depth filters include CUNO® Zeta PLUS® Delipid filters, CUNO® Emphaze AEX filters, CUNO® 30/60ZA filters, CUNO® 90ZB08A filters, CUNO® DELI08A Delipid filters, and CUNO® DELIPO8A Delipid plus filters (3M, St. Paul, Minn.), Clarisolve® grade 60HX, 40 MS, 20 MS, Milistak+® HC grade COHC, DOHC, A1HC, BIHC, XOHC, FOHC, Milistak+® HC Pro grade DOSP, COSP, and XOSP Millipor filters (EMD Millipore, Billerica, Mass.), and Sartopore® bi-layer filter cartridges.

"Tangential flow filtration", "TFF" (also called cross-flow microfiltration), and the like are terms of art, that refer to a mode of filtration in which the solute-containing solution passes tangentially across the ultrafiltration membrane and lower molecular weight salts or solutes are passed through by applying pressure.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Where embodiments of the disclosure are described in terms of a Markush group or other grouping of alternatives, the disclosed method encompasses not only the entire group listed as a whole, but also each member of the group individually and all possible subgroups of the main group, and also the main group absent one or more of the group members. The disclosed methods also envisage the explicit exclusion of one or more of any of the group members in the disclosed methods.

Methods for Clarification

In some embodiments, the disclosure provides methods for the clarification of a feed containing recombinant adeno-associated virus (rAAV) particles and an impurity, comprising (a) contacting the feed with a primary depth filter to generate a primary filtrate comprising the rAAV particles, (b) contacting the primary filtrate with a secondary depth filter to generate a secondary filtrate comprising the rAAV particles; and (c) recovering the secondary filtrate. In some embodiments, a method disclosed herein further comprises (d) contacting the secondary filtrate with a tertiary filter to generate a tertiary filtrate comprising the rAAV particles, and (e) recovering the tertiary filtrate. In some embodiments, (i) the feed comprises a cell culture, a cell lysate, or a combination thereof, (ii) the impurity comprises cells or cellular debris, and (iii) the method separates the rAAV particles from the impurity without the use of centrifugation or tangential flow microfiltration prior to (a). In some embodiments, the primary filtrate is directly loaded to the secondary depth filter. In some embodiments, the method comprises recovering the primary filtrate before being loaded to the secondary depth filter. In some embodiments, the secondary filtrate is directly loaded to the tertiary filter. In some embodiments, the method comprises recovering the secondary filtrate before being loaded to the tertiary filter. As used herein, the term "the primary filtrate is directly loaded to the secondary depth filter" refers to a process where the outlet of the primary filter is connected to the inlet of the secondary filter.

In some embodiments, the primary depth filter comprises a porous depth filter media comprising at least 2 graded layers of non-woven fibers having a total thickness of about 0.3 cm to about 3 cm, and wherein each of the at least 2 graded layers of non-woven fibers have a nominal pore size rating more than about 40 µm. In some embodiments, the primary depth filter comprises a porous depth filter media comprising at least 2 graded layers of non-woven fibers having a total thickness of about 0.3 cm to about 3 cm, and wherein each of the at least 2 graded layers of non-woven fibers have a nominal pore size rating more than about 60 µm. In some embodiments, the porous depth filter media is anisotropic. In some embodiments, the porous depth filter media comprises at least 3 graded layers of non-woven fibers. In some embodiments, the porous depth filter media comprises a composite of graded layers of non-woven fibers, cellulose, and diatomaceous earth. In some embodiments, the non-woven fibers comprise polypropylene, polyethylene, polyester, nylon, or a combination thereof. Suitable filters are known in the art, for example, as disclosed in U.S. Pat. Appl. Pub. No. 20130012689, which is incorporated herein by reference in its entirety.

In some embodiments, the porous depth filter media has an open nominal pore size rating between about 60 µm and about 0.5 µm. In some embodiments, the porous depth filter media has an open nominal pore size rating between about 50 µm and about 0.5 µm. In some embodiments, the porous depth filter media has an open nominal pore size rating between about 40 µm and about 0.5 µm. In some embodiments, the porous depth filter media has an open nominal pore size rating between about 30 µm and about 0.5 µm. In some embodiments, the porous depth filter media has an open nominal pore size rating between about 25 µm and about 0.5 µm. In some embodiments, the porous depth filter media has an open nominal pore size rating between about 20 µm and about 0.5 µm. In some embodiments, the porous depth filter media has an open nominal pore size rating between about 18 µm and about 0.6 µm.

In some embodiments, the porous depth filter media is Clarisolve® 20 MS.

In additional embodiments, the secondary depth filter comprises a media comprising a composite of cellulose and diatomaceous earth. In some embodiments, the secondary depth filter comprises a media comprising a first layer of a composite of cellulose and diatomaceous earth and a second layer of a composite of cellulose and diatomaceous earth. In some embodiments, the first layer has an open nominal pore size rating between about 5 µm and about 0.5 µm and the second layer has an open nominal pore size rating between about 0.8 µm and about 0.1 µm. In some embodiments, the first layer has an open nominal pore size rating between about 2 µm and about 0.5 µm and the second layer has an open nominal pore size rating between about 0.5 µm and about 0.1 µm. In some embodiments, the first layer has an open nominal pore size rating of about 1.2 µm and the second layer has an open nominal pore size rating of about 0.2 µm. In some embodiments, the secondary depth filter comprises a media having an open nominal pore size rating between about 5 µm and about 0.1 µm. In some embodiments, the secondary depth filter comprises a media having an open nominal pore size rating between about 2 µm and about 0.1 µm. In some embodiments, the secondary depth filter comprises a media having an open nominal pore size rating between about 1.2 µm and about 0.1 µm. Suitable filters are known in the art, for example, as disclosed in U.S. Pat. Appl. Pub. No. 20120006751, which is incorporated herein by reference in its entirety.

In some embodiments, the secondary depth filter comprises Millistak+® COHC.

In additional embodiments, the tertiary filter comprises a sterilizing grade filter media.

In some embodiments, the tertiary filter comprises polyethersulfone (PES). In some embodiments, the tertiary filter comprises polyvinylidene fluoride (PVDF). In some embodiments, the tertiary filter comprises a media comprising a hydrophilic heterogeneous double layer design. In some embodiments, the tertiary filter comprises media comprising a hydrophilic heterogeneous double layer design of a 0.8 µm pre-filter and 0.2 µm final filter membrane. In some embodiments, the tertiary filter comprises media comprising a hydrophilic heterogeneous double layer design of a 1.2 µm pre-filter and 0.2 µm final filter membrane.

In some embodiments, the tertiary filter is a 0.2 or 0.22 µm pore filter. In further embodiments, the sterilizing filter is a 0.2 µm pore filter. In some embodiments, the sterilizing filter is a Sartopore® 2 XLG 0.2 µm, Durapore™ PVDF Membranes 0.45 µm, or Sartoguard® PES 1.2 µm+0.2 µm nominal pore size combination. In some embodiments, the tertiary filter is a Sartopore® 2 XLG 0.2 µm. In some embodiments, the tertiary filter is a 0.1 µm pore filter. In some embodiments, the tertiary filter has a pore size between about 0.2 µm and about 0.1 µm.

In additional embodiments, the ratio of primary filter area to secondary filter area is between about 1:5 and about 5:1. In some embodiments, the ratio of primary filter area to secondary filter area is between about 1:4 and about 4:1. In some embodiments, the ratio of primary filter area to secondary filter area is between about 1:3 and about 3:1. In some embodiments, the ratio of primary filter area to secondary filter area is between about 1:2 and about 2:1. In some embodiments, the ratio of primary filter area to secondary filter area is about 5:1, about 4:1, about 3:1, about 2:1, about 1:1, about 1:2, about 1:3, about 1:4, or about 1:5. In some embodiments, the ratio of primary filter area to secondary filter area is about 1:2. In some embodiments, the ratio of primary filter area to secondary filter area is about 2:1. In some embodiments, the ratio of primary filter area to secondary filter area is about 1:1.

In additional embodiments, the ratio of primary filter area to tertiary filter area is between about 1:5 and about 5:1. In some embodiments, the ratio of primary filter area to tertiary filter area is between about 1:4 and about 4:1. In some embodiments, the ratio of primary filter area to tertiary filter area is between about 1:3 and about 3:1. In some embodiments, the ratio of primary filter area to tertiary filter area is between about 1:2 and about 2:1. In some embodiments, the ratio of primary filter area to tertiary filter area is about 5:1, about 4:1, about 3:1, about 2:1, about 1:1, about 1:2, about 1:3, about 1:4, or about 1:5. In some embodiments, the ratio of primary filter area to tertiary filter area is about 1:2. In some embodiments, the ratio of primary filter area to tertiary filter area is about 2:1. In some embodiments, the ratio of primary filter area to tertiary filter area is about 1:1.

In additional embodiments, the ratio of secondary filter area to tertiary filter area is between about 1:5 and about 5:1. In some embodiments, the ratio of secondary filter area to tertiary filter area is between about 1:4 and about 4:1. In some embodiments, the ratio of secondary filter area to tertiary filter area is between about 1:3 and about 3:1. In some embodiments, the ratio of secondary filter area to tertiary filter area is between about 1:2 and about 2:1. In some embodiments, the ratio of secondary filter area to tertiary filter area is about 5:1, about 4:1, about 3:1, about 2:1, about 1:1, about 1:2, about 1:3, about 1:4, or about 1:5. In some embodiments, the ratio of secondary filter area to tertiary filter area is about 1:2. In some embodiments, the ratio of secondary filter area to tertiary filter area is about 2:1. In some embodiments, the ratio of secondary filter area to tertiary filter area is about 1:1.

In additional embodiments, the ratio of primary filter area to secondary filter area to tertiary filter area ratio is within the range of about 0.3-3 to about 0.3-3 to about 0.2-5. In some embodiments, the ratio of primary filter area to secondary filter area to tertiary filter area ratio is within the range of about 0.3-3 to about 1 to about 0.2-5. In some embodiments, the ratio of primary filter area to secondary filter area to tertiary filter area ratio is about 2 to about 1 to about 1. In some embodiments, the ratio of primary filter area to secondary filter area to tertiary filter area ratio is about 1 to about 1 to about 1. In some embodiments, the ratio of primary filter area to secondary filter area to tertiary filter area ratio is about 8 to about 5 to about 4. In some embodiments, the flux through the primary and secondary filters is between about 150 LMH and about 250 LMH. In some embodiments, the flux is between about 175 LMH and about 225 LMH. In some embodiments, the flux is between about 190 LMH and about 210 LMH. In some embodiments, the flux is about 225 LMH. In some embodiments, the flux is about 200 LMH. In some embodiments, the flux is about 50 LMH.

In additional embodiments, the flux through the primary, secondary, and tertiary filters is between about 150 LMH and about 250 LMH. In some embodiments, the flux is between about 175 LMH and about 225 LMH. In some embodiments, the flux is between about 190 LMH and about 210 LMH. In some embodiments, the flux is about 225 LMH. In some embodiments, the flux is about 200 LMH. In some embodiments, the flux is about 50 LMH.

In additional embodiments, the provided clarification method comprises pretreating the feed before contacting the feed with the primary depth filter.

In some embodiments, the pretreating comprises adding a salt to the feed. As used herein, the term "salt" refers to a compound formed by the interaction of an acid and a base. Various salts which may be used in the methods described herein include, but are not limited to, acetate (e.g. sodium acetate), citrate (e.g., sodium citrate), chloride (e.g., sodium chloride), sulphate (e.g., sodium sulphate), or a potassium salt (e.g., potassium chloride). In some embodiments, the pretreating comprises adding a salt to the feed to a final concentration between about 0.2 M and about 0.6 M. In some embodiments, the pretreating comprises adding a salt to a final concentration of about 0.2 M, about 0.3 M, about 0.4 M, about 0.5 M, or about 0.6 M. In some embodiments, the pretreating comprises adding a salt to a final concentration of about 0.3 M. In some embodiments, the pretreating comprises adding a salt to a final concentration of about 0.5

M. In some embodiments, the salt is sodium citrate, sodium chloride, or sodium sulphate. In some embodiments, the salt is sodium chloride. In other embodiments, the pretreating does not include adding a salt to the feed.

In some embodiments, the pretreating comprises adding a chemical flocculent to the feed. Flocculents are a class of materials that can aggregate and agglutinate fine particles from a solution, resulting in their settling from the liquid phase and a reduction in solution turbidity. Suitable flocculents are known in the art, for example, as disclosed in U.S. Pat. Appl. Pub. No. 20130012689, which is incorporated herein by reference in its entirety. In some embodiments, the chemical flocculent is a polymer, including, but not limited to a smart polymer (e.g., a modified polyamine). In some embodiments, the chemical flocculent is an acid (e.g., acetic acid).

In some embodiments, the feed is not pre-treated before contacting the feed with the primary depth filter.

The provided methods produce a clarified feed without the upstream use of centrifugation or tangential flow microfiltration. In some embodiments, the clarified feed has a turbidity of less than about 50 NTU, less than about 25 NTU, less than about 10 NTU, less than about 5 NTU, less than about 3 NTU, or less than about 2 NTU. In some embodiments, the turbidity of the secondary filtrate is less than about 50 NTU. In some embodiments, the turbidity of the secondary filtrate is less than about 25 NTU. In some embodiments, the turbidity of the secondary filtrate is less than about 10 NTU. In some embodiments, the turbidity of the secondary filtrate is less than about 5 NTU. In some embodiments, the turbidity of the secondary filtrate is less than about 3 NTU. In some embodiments, the turbidity of the secondary filtrate is less than about 2 NTU. In some embodiments, the turbidity of the tertiary filtrate is less than about 50 NTU. In some embodiments, the turbidity of the tertiary filtrate is less than about 25 NTU. In some embodiments, the turbidity of the tertiary filtrate is less than about 10 NTU. In some embodiments, the turbidity of the tertiary filtrate is less than about 5 NTU. In some embodiments, the turbidity of the tertiary filtrate is less than about 3 NTU. In some embodiments, the turbidity of the tertiary filtrate is less than about 2 NTU.

The provided methods produce a clarified feed without significant losses of rAAV. In some embodiments, the yield of rAAV particles in the secondary filtrate is at least about 50%. In some embodiments, the yield of rAAV particles in the secondary filtrate is at least about 60%. In some embodiments, the yield of rAAV particles in the secondary filtrate is at least about 70%. In some embodiments, the yield of rAAV particles in the secondary filtrate is at least about 80%. In some embodiments, the yield of rAAV particles in the secondary filtrate is at least about 90%. In some embodiments, the yield of rAAV particles in the secondary filtrate is at least about 95%. In some embodiments, the yield of rAAV particles in the secondary filtrate is at least about 96%. In some embodiments, the yield of rAAV particles in the secondary filtrate is at least about 97%. In some embodiments, the yield of rAAV particles in the secondary filtrate is at least about 98%. In some embodiments, the yield of rAAV particles in the secondary filtrate is at least about 99%. In some embodiments, the yield of rAAV particles in the tertiary filtrate is at least about 50%. In some embodiments, the yield of rAAV particles in the tertiary filtrate is at least about 60%. In some embodiments, the yield of rAAV particles in the tertiary filtrate is at least about 70%. In some embodiments, the yield of rAAV particles in the tertiary filtrate is at least about 80%. In some embodiments, the yield of rAAV particles in the tertiary filtrate is at least about 90%. In some embodiments, the yield of rAAV particles in the tertiary filtrate is at least about 95%. In some embodiments, the yield of rAAV particles in the tertiary filtrate is at least about 96%. In some embodiments, the yield of rAAV particles in the tertiary filtrate is at least about 97%. In some embodiments, the yield of rAAV particles in the tertiary filtrate is at least about 98%. In some embodiments, the yield of rAAV particles in the tertiary filtrate is at least about 99%.

Production of rAAV Particles

The provided methods are suitable for use in the production of any isolated recombinant AAV particles. As such, the rAAV in the clarified feed produced according to the disclosed may be of any serotype, modification, or derivative, known in the art, or any combination thereof (e.g., a population of rAAV particles that comprises two or more serotypes, e.g., comprising two or more of rAAV2, rAAV8, and rAAV9 particles) known in the art. In some embodiments, the rAAV particles are AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other rAAV particles, or combinations of two or more thereof.

In some embodiments, rAAV particles have a capsid protein from an AAV serotype selected from AAV1, AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, rAAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise a capsid protein from an AAV capsid serotype selected from AAV1, AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16, or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise the capsid of Anc80 or Anc80L65, as described in Zinn et al., 2015, Cell Rep. 12(6): 1056-1068, which is incorporated by reference in its entirety. In certain embodiments, the rAAV particles comprise the capsid with one of the following amino acid insertions: LGETTRP (SEQ ID NO: 1) or LALGETTRP (SEQ ID NO: 2), as described in U.S. Pat. Nos. 9,193,956; 9,458,517; and 9,587,282 and US patent application publication no. 2016/0376323, each of which is incorporated herein by reference in its entirety. In some embodiments, rAAV particles comprise the capsid of AAV.7m8, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise any AAV capsid disclosed in U.S. Pat. No. 9,585,971, such as AAV-PHP.B. In some embodiments, rAAV particles comprise any AAV capsid disclosed in U.S. Pat. No. 9,840,719 and WO 2015/013313, such as AAV.Rh74 and RHM4-1, each of which is incorporated herein by reference in its entirety. In some embodiments, rAAV particles comprise any AAV capsid disclosed in WO 2014/172669, such as AAV rh.74, which is incorporated herein by reference in its entirety. In some embodiments, rAAV particles comprise the capsid of AAV2/5, as described in Georgiadis et al., 2016, Gene Therapy 23: 857-862 and Georgiadis et al., 2018, Gene Therapy 25: 450, each of which is incorporated by reference in its entirety. In some embodiments, rAAV particles comprise any AAV capsid disclosed in WO 2017/070491, such as AAV2tYF, which is incorporated herein by reference in its entirety. In some embodiments, rAAV particles comprise the capsids of AAVLK03 or AAV3B, as described in Puzzo et al., 2017, Sci. Transl. Med. 29(9): 418, which is incorporated by reference in its entirety. In some embodiments, rAAV particles comprise any AAV capsid disclosed in U.S. Pat. Nos. 8,628,966; 8,927,514; 9,923,120 and WO 2016/049230, such as HSC1, HSC2, HSC3, HSC4, HSC5, HSC6, HSC7, HSC8, HSC9, HSC10, HSC11, HSC12, HSC13, HSC14, HSC15, or HSC16, each of which is incorporated by reference in its entirety.

In some embodiments, rAAV particles comprise an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335.

In some embodiments, rAAV particles have a capsid protein disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689, (see, e.g., SEQ ID NOs: 5-38) WO2009/104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10), the contents of each of which is herein incorporated by reference in its entirety. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689 (see, e.g., SEQ ID NOs: 5-38) WO2009/104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10).

Nucleic acid sequences of AAV based viral vectors and methods of making recombinant AAV and AAV capsids are taught, for example, in U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; International Patent Application Nos. PCT/US2015/034799; PCT/EP2015/053335; WO 2003/052051, WO 2005/033321, WO 03/042397, WO 2006/068888, WO 2006/110689, WO2009/104964, WO 2010/127097, and WO 2015/191508, and U.S. Appl. Publ. No. 20150023924.

The provided methods are suitable for used in the production of recombinant AAV encoding a transgene. In some embodiments, provided herein are rAAV viral vectors encoding an anti-VEGF Fab. In specific embodiments, provided herein are rAAV8-based viral vectors encoding an anti-VEGF Fab. In more specific embodiments, provided herein are rAAV8-based viral vectors encoding ranibizumab. In some embodiments, provided herein are rAAV viral vectors encoding Iduronidase (IDUA). In specific embodiments, provided herein are rAAV9-based viral vectors encoding IDUA. In some embodiments, provided herein are rAAV viral vectors encoding Iduronate 2-Sulfatase (IDS). In specific embodiments, provided herein are rAAV9-based viral vectors encoding IDS. In some embodiments, provided herein are rAAV viral vectors encoding a low-density lipoprotein receptor (LDLR). In specific embodiments, provided herein are rAAV8-based viral vectors encoding LDLR. In some embodiments, provided herein are rAAV viral vectors encoding tripeptidyl peptidase 1 (TPP1) protein. In specific embodiments, provided herein are rAAV9-based viral vectors encoding TPP.

In additional embodiments, rAAV particles comprise a pseudotyped AAV capsid. In some embodiments, the pseudotyped AAV capsids are rAAV2/8 or rAAV2/9 pseudo-typed AAV capsids. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles comprise a capsid containing a capsid protein chimeric of two or more AAV capsid serotypes. In some embodiments, the capsid protein is a chimeric of 2 or more AAV capsid proteins from AAV serotypes selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In certain embodiments, a single-stranded AAV (ssAAV) can be used. In certain embodiments, a self-complementary vector, e.g., scAAV, can be used (see, e.g., Wu, 2007, Human Gene Therapy, 18(2): 171-82, McCarty et al, 2001, Gene Therapy, Vol. 8, Number 16, Pages 1248-1254; and U.S. Pat. Nos. 6,596,535; 7,125,717; and 7,456,683, each of which is incorporated herein by reference in its entirety).

In some embodiments, rAAV particles in the clarified feed comprise a capsid protein from an AAV capsid serotype selected from AAV-8 or AAV-9. In some embodiments, the rAAV particles have an AAV capsid serotype of AAV-1 or a derivative, modification, or pseudotype thereof. In some embodiments, the rAAV particles have an AAV capsid serotype of AAV-4 or a derivative, modification, or pseudotype thereof. In some embodiments, the rAAV particles have an AAV capsid serotype of AAV-5 or a derivative, modification, or pseudotype thereof. In some embodiments, the rAAV particles have an AAV capsid serotype of AAV-8 or a derivative, modification, or pseudotype thereof. In some embodiments, the rAAV particles have an AAV capsid serotype of AAV-9 or a derivative, modification, or pseudotype thereof.

In some embodiments, rAAV particles in the clarified feed comprise a capsid protein that is a derivative, modification, or pseudotype of AAV-8 or AAV-9 capsid protein. In some embodiments, rAAV particles in the clarified feed comprise a capsid protein that has an AAV-8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-8 capsid protein.

In some embodiments, rAAV particles in the clarified feed comprise a capsid protein that is a derivative, modification, or pseudotype of AAV-9 capsid protein. In some embodiments, rAAV particles in the clarified feed comprise a capsid protein that has an AAV-8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-9 capsid protein.

In additional embodiments, rAAV particles in the clarified feed comprise a mosaic capsid. Mosaic AAV particles are composed of a mixture of viral capsid proteins from different serotypes of AAV. In some embodiments, rAAV particles in the clarified feed comprise a mosaic capsid containing capsid proteins of a serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, rAAV particles in the clarified feed comprise a mosaic capsid containing capsid proteins of a serotype selected from AAV-1, AAV-2, AAV-5, AAV-6, AAV-7, AAV-8, AAV-9, AAV-10, AAVrh.8, and AAVrh.10.

In additional embodiments, rAAV particles in the clarified feed comprise a pseudotyped rAAV particle. In some embodiments, the pseudotyped rAAV particle comprises (a) a nucleic acid vector comprising AAV ITRs and (b) a capsid comprised of capsid proteins derived from AAVx (e.g., AAV-1, AAV-3, AAV-4, AAV-5, AAV-6, AAV-7, AAV-8, AAV-9, AAV-10 AAV-11, AAV-12, AAV-13, AAV-14, AAV-15 and AAV-16). In additional embodiments, rAAV particles in the clarified feed comprise a pseudotyped rAAV particle comprised of a capsid protein of an AAV serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In additional embodiments, rAAV particles in the clarified feed comprise a pseudotyped rAAV particle containing AAV-8 capsid protein. In additional embodiments, rAAV particles in the clarified feed comprise a pseudotyped rAAV particle is comprised of AAV-9 capsid protein. In some embodiments, the pseudotyped rAAV8 or rAAV9 particles are rAAV2/8 or rAAV2/9 pseudotyped particles. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles in the clarified feed comprise a capsid containing a capsid protein chimeric of two or more AAV capsid serotypes. In further embodiments, the capsid protein is a chimeric of 2 or more AAV capsid proteins from AAV serotypes selected from AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, rAAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In further embodiments, the capsid protein is a chimeric of 2 or more AAV capsid proteins from AAV serotypes selected from AAV-1, AAV-2, AAV-5, AAV-6, AAV-7, AAV-8, AAV-9, AAV-10, AAVrh.8, and AAVrh. 10.

In some embodiments, the rAAV particles comprise an AAV capsid protein chimeric of AAV-8 capsid protein and one or more AAV capsid proteins from an AAV serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise an AAV capsid protein chimeric of AAV-8 capsid protein and one or more AAV capsid proteins from an AAV serotype selected from AAV-1, AAV-2, AAV-5, AAV-6, AAV-7, AAV-9, AAV-10, AAVrh.8, and AAVrb.10.

In some embodiments, the rAAV particles comprise an AAV capsid protein chimeric of AAV-9 capsid protein the capsid protein of one or more AAV capsid serotypes selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, the rAAV particles comprise an AAV capsid protein chimeric of AAV-9 capsid protein the capsid protein of one or more AAV capsid serotypes selected from AAV1, AAV2, AAV3, AAV4, AAV5, AA6, AAV7, AAV8, AAV9, AAVrh.8, and AAVrb.10.

Numerous methods are known in the art for production of rAAV particles, including transfection, stable cell line production, and infectious hybrid virus production systems which include Adenovirus-AAV hybrids, herpesvirus-AAV hybrids and baculovirus-AAV hybrids. rAAV production cultures for the production of rAAV virus particles all require; (1) suitable host cells, including, for example, human-derived cell lines such as HeLa, A549, or HEK293 cells, or insect-derived cell lines such as SF-9, in the case of baculovirus production systems; (2) suitable helper virus function, provided by wild type or mutant adenovirus (such as temperature sensitive adenovirus), herpes virus, baculovirus, or a plasmid construct providing helper functions; (3) AAV rep and cap genes and gene products; (4) a transgene (such as a therapeutic transgene) flanked by AAV ITR sequences; and (5) suitable media and media components to support rAAV production. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), and Sf-900 II SFM media as described in U.S. Pat. No. 6,723,551, which is incorporated herein by reference in its entirety.

rAAV production cultures can routinely be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

A feed comprising rAAV particles can be harvested from rAAV production cultures by harvest of the production culture comprising host cells or by harvest of the spent media from the production culture, provided the cells are cultured under conditions known in the art to cause release of rAAV particles into the media from intact host cells. A feed comprising rAAV particles can also be harvested from rAAV production cultures by lysis of the host cells of the production culture. Suitable methods of lysing cells are also known in the art and include for example multiple freeze/thaw cycles, sonication, microfluidization, and treatment with chemicals, such as detergents and/or proteases.

In some embodiments, the rAAV production culture harvest is treated with a nuclease (e.g., Benzonase®) or endonuclease (e.g., endonuclease from *Serratia marcescens*) to digest high molecular weight DNA present in the production culture. The nuclease or endonuclease digestion can routinely be performed under standard conditions known in the art. For example, nuclease digestion is performed at a final concentration of 1-2.5 units/ml of Benzonase® at a temperature ranging from ambient to 37° ° C. for a period of 30 minutes to several hours.

In some embodiments, the feed containing rAAV particles comprises a high density cell culture. In some embodiments, the culture has a total cell density of between about 1×10E+06 cells/ml and about 30×10E+06 cells/ml. In some embodiments, the culture has a total cell density of between about 5×10E+06 cells/ml and about 25×10E+06 cells/ml. In some embodiments, the culture has a total cell density of between about 10×10E+06 cells/ml and about 20×10E+06 cells/ml. In some embodiments, the culture has a total cell density of about 10×10E+06 cells/ml, about 11×10E+06 cells/ml, about 12×10E+06 cells/ml, about 13×10E+06 cells/ml, about 14×10E+06 cells/ml, about 14×10E+06 cells/ml, about 15×10E+06 cells/ml, about 16×10E+06 cells/ml, about 17×10E+06 cells/ml, about 18×10E+06 cells/ml, about 19×10E+06 cells/ml, about 20×10E+06 cells/ml. In some embodiments, the culture has a total cell density of at least about 10×10E+06 cells/ml, at least about 11×10E+06 cells/ml, at least about 12×10E+06 cells/ml, at least about 13×10E+06 cells/ml, at least about 14×10E+06 cells/ml, at least about 14×10E+06 cells/ml, at least about 15×10E+06 cells/ml, at least about 16×10E+06 cells/ml, at least about 17×10E+06 cells/ml, at least about 18×10E+06 cells/ml, at least about 19×10E+06 cells/ml, at least about 20×10E+06 cells/ml. In some embodiments, between about 40% and about 90% of the cells are viable cells. In some embodiments, between about between about 60% and about 80% of the cells are viable cells. In some embodiments, more than about 50% of the cells are viable cells. In some embodiments, more than about 60% of the cells are viable cells. In some embodiments, more than about 70% of the cells are viable cells. In some embodiments, the cells are Hela cells, HEK293 cells, or SF-9 cells. In further embodiments, the cells are HEK293 cells. In further embodiments, the cells are HEK293 cells adapted for growth in suspension culture.

In some embodiments, the culture has a viable cell density of between about 1×10E+06 cells/ml and about 30×10E+06 cells/ml. In some embodiments, the culture has a viable cell density of between about 5×10E+06 cells/ml and about 25×10E+06 cells/ml. In some embodiments, the culture has a viable cell density of between about 10×10E+06 cells/ml and about 20×10E+06 cells/ml. In some embodiments, the culture has a viable cell density of about 6×10E+06 cells/ml, about 7×10E+06 cells/ml, about 8×10E+06 cells/ml, about 9×10E+06 cells/ml, about 10×10E+06 cells/ml, about 11×10E+06 cells/ml, about 12×10E+06 cells/ml, about 13×10E+06 cells/ml, about 14×10E+06 cells/ml, about 14×10E+06 cells/ml, about 15×10E+06 cells/ml, or about 16×10E+06 cells/ml. In some embodiments, the culture has a viable cell density of at least about 6×10E+06 cells/ml, at least about 7×10E+06 cells/ml, at least about 8×10E+06 cells/ml, at least about 9×10E+06 cells/ml, at least about 10×10E+06 cells/ml, at least about 11×10E+06 cells/ml, at least about 12×10E+06 cells/ml, at least about 13×10E+06 cells/ml, at least about 14×10E+06 cells/ml, at least about 14×10E+06 cells/ml, at least about 15×10E+06 cells/ml, or at least about 16×10E+06 cells/ml. In some embodiments, the cells are Hela cells, HEK293 cells, or SF-9 cells. In some embodiments, the cells are HEK293 cells. In further embodiments, the cells are HEK293 cells adapted for growth in suspension culture.

In additional embodiments of the provided method for clarifying a feed containing rAAV particles, the feed comprises a suspension culture comprising rAAV particles. Numerous suspension cultures are known in the art for production of rAAV particles, including for example, the cultures disclosed in U.S. Pat. Nos. 6,995,006, 9,783,826, and in U.S. Pat. Appl. Pub. No. 20120122155, each of which is incorporated herein by reference in its entirety. In some embodiments, the suspension culture comprises a culture of HeLa cells, HEK293 cells, or SF-9 cells. In some embodiments, the suspension culture comprises a culture of HEK293 cells.

In additional embodiments of the provided method for clarifying a feed containing rAAV particles, the primary filter has a capacity of between about 50 L/m$^2$ and about 400 L/m$^2$ at 200 LMH. In some embodiments, the primary filter has a capacity of between about 200 L/m$^2$ and about 400 L/m$^2$. In some embodiments, the primary filter has a capacity of between about 200 L/m$^2$ and about 300 L/m$^2$. In some embodiments, the primary filter has a capacity of between about 100 L/m$^2$ and about 250 L/m$^2$. In some embodiments, the primary filter has a capacity of between about 150 L/m$^2$ and about 250 L/m$^2$. In some embodiments, the primary filter has a capacity of between about 150 L/m$^2$ and about 200 L/m$^2$. In some embodiments, the primary filter has a capacity of between about 160 L/m$^2$ and about 290 L/m$^2$. In some embodiments, the primary filter has a capacity of about 150 L/m$^2$. In some embodiments, the primary filter has a capacity of about 160 L/m$^2$. In some embodiments, the primary filter has a capacity of about 170 L/m$^2$. In some embodiments, the primary filter has a capacity of about 175 L/m$^2$. In some embodiments, the primary filter has a capacity of about 180 L/m$^2$. In some embodiments, the primary filter has a capacity of about 190 L/m$^2$. In some embodiments, the primary filter has a capacity of about 200 L/m$^2$. In some embodiments, the primary filter has a capacity higher than about 200 L/m$^2$. In some embodiments, the primary filter has a capacity higher than about 225 L/m$^2$. In some embodiments, the primary filter has a capacity higher than about 250 L/m$^2$. In some embodiments, filter capacity is determined using a constant flow method. In some embodiments, filter capacity is the volume of feed per filter area at which the filter reaches its clogging point. In some embodiments, filter capacity is the volume of feed per filter area at which the pressure of the filter reaches 25 psig. In some embodiments, filter capacity is the volume of feed per filter area at which the filtrate flow rate has decreased to ≤30% of the feed flow rate. In some embodiments, filter capacity is determined with a feed comprising a cell culture that has a total cell density of between about 1×10E+06 cells/ml and about 30×10E+06 cells/ml. In some embodiments, filter capacity is determined with a feed comprising a cell culture, wherein between about 60% and about 80% of the cells in the culture are viable cells. In some embodiments, filter capacity is determined with a feed comprising a cell culture, wherein >60% of the cells in the culture are viable cells.

In additional embodiments of the provided method for clarifying a feed containing rAAV particles, the secondary filter has a capacity of between about 200 L/m$^2$ and about 650 L/m$^2$ at 200 LMH. In some embodiments, the secondary filter has a capacity of between about 250 L/m$^2$ and about 650 L/m$^2$. In some embodiments, the secondary filter has a capacity of between about 350 L/m$^2$ and about 550 L/m$^2$. In some embodiments, the secondary filter has a capacity of between about 400 L/m$^2$ and about 500 L/m$^2$. In some embodiments, the secondary filter has a capacity of between about 450 L/m$^2$ and about 550 L/m$^2$. In some embodiments, the secondary filter has a capacity of between about 400 L/m$^2$ and about 600 L/m$^2$. In some embodiments, the secondary filter has a capacity of between about 500 L/m$^2$ and about 600 L/m$^2$. In some embodiments, the secondary filter has a capacity of between about 250 L/m$^2$ and about 350 L/m$^2$. In some embodiments, the secondary filter has a capacity of between about 250 L/m$^2$ and about 300 L/m$^2$. In some embodiments, the secondary filter has a capacity of about 250 L/m$^2$. In some embodiments, the secondary filter has a capacity of about 270 L/m$^2$. In some embodiments, the secondary filter has a capacity of about 280 L/m$^2$. In some embodiments, the secondary filter has a capacity of about 290 L/m$^2$. In some embodiments, the secondary filter has a capacity of about 300 L/m$^2$. In some embodiments, the secondary filter has a capacity of about 350 L/m$^2$. In some embodiments, the secondary filter has a capacity of about 400 L/m$^2$. In some embodiments, the secondary filter has a capacity of about 450 L/m$^2$. In some embodiments, the secondary filter has a capacity of about 500 L/m$^2$. In some embodiments, the secondary filter has a capacity of more than about 250 L/m$^2$ at 200 LMH. In some embodiments, the secondary filter has a capacity of more than about 270 L/m$^2$. In some embodiments, the secondary filter has a capacity of more than about 280 L/m$^2$. In some embodiments, the secondary filter has a capacity of more than about 400 L/m$^2$.

In some embodiments, the secondary filter has a capacity of more than about 450 L/m². In some embodiments, the secondary filter has a capacity of more than about 500 L/m². In some embodiments, filter capacity is determined using a constant flow method. In some embodiments, filter capacity is the volume of feed per filter area at which the filter reaches its clogging point. In some embodiments, filter capacity is the volume of feed per filter area at which the pressure of the filter reaches 25 psig. In some embodiments, filter capacity is the volume of feed per filter area at which the filtrate flow rate has decreased to ≤30% of the feed flow rate. In some embodiments, filter capacity is determined with a feed comprising the primary filtrate.

In additional embodiments of the provided method for clarifying a feed containing rAAV particles, the tertiary filter has a capacity of between about 400 L/m² and about 2500 L/m² at 200 LMH. In some embodiments, the tertiary filter has a capacity of between about 450 L/m² and about 900 L/m². In some embodiments, the tertiary filter has a capacity of between about 450 L/m² and about 550 L/m². In some embodiments, the tertiary filter has a capacity of between about 400 L/m² and about 600 L/m². In some embodiments, the tertiary filter has a capacity of between about 700 L/m² and about 900 L/m². In some embodiments, the tertiary filter has a capacity of between about 750 L/m² and about 850 L/m². In some embodiments, the tertiary filter has a capacity of about 400 L/m². In some embodiments, the tertiary filter has a capacity of about 450 L/m². In some embodiments, the tertiary filter has a capacity of about 500 L/m². In some embodiments, the tertiary filter has a capacity of about 550 L/m². In some embodiments, the tertiary filter has a capacity of about 600 L/m². In some embodiments, the tertiary filter has a capacity of about 650 L/m². In some embodiments, the tertiary filter has a capacity of about 700 L/m². In some embodiments, the tertiary filter has a capacity of about 750 L/m². In some embodiments, the tertiary filter has a capacity of about 800 L/m². In some embodiments, the tertiary filter has a capacity of about 850 L/m². In some embodiments, the tertiary filter has a capacity of about 900 L/m². In some embodiments, the tertiary filter has a capacity of more than about 400 L/m² at 200 LMH. In some embodiments, the tertiary filter has a capacity of more than about 450 L/m². In some embodiments, the tertiary filter has a capacity of more than about 500 L/m². In some embodiments, the tertiary filter has a capacity of more than about 600 L/m². In some embodiments, the tertiary filter has a capacity of more than about 700 L/m². In some embodiments, the tertiary filter has a capacity of more than about 800 L/m². In some embodiments, filter capacity is determined using a constant flow method. In some embodiments, filter capacity is the volume of feed per filter area at which the filter reaches its clogging point. In some embodiments, filter capacity is the volume of feed per filter area at which the pressure of the filter reaches 25 psig. In some embodiments, filter capacity is the volume of feed per filter area at which the filtrate flow rate has decreased to ≤30% of the feed flow rate. In some embodiments, filter capacity is determined with a feed comprising the secondary filtrate.

In additional embodiments of the provided method for clarifying a feed containing rAAV particles, the primary filter has a capacity of between about 150 L/m² and about 2400 L/m², the secondary filter has a capacity of more than about 280 L/m², and the tertiary filter has a capacity of more than about 350 L/m² at 200 LMH. In some embodiments, the primary filter has a capacity of about 175 L/m², the secondary filter has a capacity of more than about 280 L/m², and the tertiary filter has a capacity of more than about 350 L/m² at 200 LMH. In some embodiments, the ratio of primary filter area to secondary filter area to tertiary filter area ratio is about 2 to about 1 to about 1. In some embodiments, the ratio of primary filter area to secondary filter area to tertiary filter area ratio is about 8 to about 5 to about 4.

In some embodiments of the methods disclosed herein large volumes of feed can be present (e.g., during the commercial manufacturing processes). Large volumes create several challenges for filter based clarification processes. For example, the effect that a small change in flow rate through a filter has on the recovery of rAAV is amplified when large volumes are used. Likewise, when using large volumes, the effect that an increase in cell density in a feed has on product recovery is also amplified. Thus, the use of large volumes of a feed present unique problems that are amplified and have greater ramifications relative to the use of smaller volumes. Thus, in some embodiments of the method of clarification disclosed herein is suitable for the processing of a large volume of a feed comprising rAAV particles. The term "large volume" refers to volumes associated with the commercial and/or industrial production of rAAV particles. In some embodiments, the term "large volume" refers to between about 50 liters and about 20,000 liters, between about 100 liters and about 20,000 liters, between about 1,000 liters and about 20,000 liters, between about 5,000 liters and about 20,000 liters, between about 10,000 liters and about 20,000 liters, between about 15,000 liters and about 20,000 liters. In some embodiments, the term "large volume" refers to between about 5,000 liters and about 10,000 liters, between about 5,000 liters and about 15,000 liters, between about 1,000 liters and about 10,000 liters, between about 5,000 liters and about 10,000 liters, between about 5,000 liters and about 15,000 liters. In some embodiments, the term "large volume" refers to between about 50 liters and about 5,000 liters, between about 100 liters and about 3,000 liters, between about 500 liters and about 3,000 liters, between about 1,500 liters and about 2,500 liters. In some embodiments, the term "large volume" refers to about 2,000 liters. In some embodiments, the term "large volume" refers to about 200 liters. In some embodiments, the term "large volume" refers to about 500 liters. In some embodiments, the term "large volume" refers to about 1,000 liters. In some embodiments, the term "large volume" refers to about 1,500 liters. In some embodiments, the term "large volume" refers to about 2,000 liters. In some embodiments, the term "large volume" refers to about 2,500 liters. In some embodiments, the term "large volume" refers to about 3,000 liters. In some embodiments, the term "large volume" refers to about 5,000 liters. In some embodiments, the term "large volume" refers to about 1,000 liters. In some embodiments, the term "large volume" refers to about 15,000 liters. In some embodiments, the term "large volume" refers to about 20,000 liters. In some embodiments, the term "large volume" refers to between about 10 liters and 1,000 liters, between about 10 liters and 100 liters, between about 20 liters and 500 liters, between about 50 liters and 500 liters, between about 100 liters and 1,000 liters, or between about 100 liters and 500 liters.

Methods for Isolating rAAV

Recombinant AAV particles in the clarified feed prepared according to the disclosed methods (e.g., the method of any one of [1]-[91]) can be isolated using methods known in the art. In some embodiments, the methods of isolating rAAV particles from the clarified feed comprise downstream use of one or more of tangential flow filtration, affinity chromatography, size exclusion chromatography, ion exchange chromatography, hydroxylapatite chromatography, and hydrophobic interaction chromatography. In some embodiments, the downstream processing includes at least 2, at least 3, or at least 4 of: tangential flow filtration, affinity chromatography, anion exchange chromatography, hydrophobic interaction chromatography, size exclusion chromatography, or sterile filtration. In some embodiments, the further downstream processing includes tangential flow filtration. In some embodiments, the downstream processing includes sterile filtration. In further embodiments, the downstream processing includes tangential flow filtration and sterile filtration.

In some embodiments, the clarified feed is concentrated via tangential flow filtration ("TFF") before being applied to a chromatographic medium, for example, affinity chromatography medium. Large scale concentration of viruses using TFF ultrafiltration has been described by Paul et al., Human Gene Therapy 4:609-615 (1993). TFF concentration of the clarified feed enables a technically manageable volume of clarified feed to be subjected to chromatography and allows for more reasonable sizing of columns without the need for lengthy recirculation times. In some embodiments, the clarified feed is concentrated between at least two-fold and at least ten-fold. In some embodiments, the clarified feed is concentrated between at least ten-fold and at least twenty-fold. In some embodiments, the clarified feed is concentrated between at least twenty-fold and at least fifty-fold. In some embodiments, the clarified feed is concentrated about twenty-fold. One of ordinary skill in the art will also recognize that TFF can also be used to remove small molecule impurities (e.g., cell culture contaminants comprising media components, serum albumin, or other serum proteins) form the clarified feed via diafiltration. In some embodiments, the clarified feed is subjected to diafiltration to remove small molecule impurities. In some embodiments, the diafiltration comprises the use of between about 3 and about 10 diafiltration volume of buffer. In some embodiments, the diafiltration comprises the use of about 5 diafiltration volume of buffer. One of ordinary skill in the art will also recognize that TFF can also be used at any step in the purification process where it is desirable to exchange buffers before performing the next step in the purification process. In some embodiments, the methods for isolating rAAV from the clarified feed disclosed herein comprise the use of TFF to exchange buffers.

Affinity chromatography can be used to isolate rAAV particles from a composition. In some embodiments, affinity chromatography is used to isolate rAAV particles from the clarified feed. In some embodiments, affinity chromatography is used to isolate rAAV particles from the clarified feed that has been subjected to tangential flow filtration. Suitable affinity chromatography media are known in the art and include without limitation, AVB Sepharose™, POROS™ CaptureSelect™ AAV9 affinity resin, CaptureSelect™ AAVX affinity resin, and POROS™ CaptureSelect™ AAV8 affinity resin. In some embodiments, the affinity chromatography media is POROS™ CaptureSelect™ AAV9 affinity resin.

Anion exchange chromatography can be used to isolate rAAV particles from a composition. In some embodiments, anion exchange chromatography is used after affinity chromatography as a final concentration and polish step. Suitable anion exchange chromatography media are known in the art and include without limitation, Unosphere Q (Biorad, Hercules, Calif.), and N-charged amino or imino resins such as e.g., POROS 50 PI, or any DEAE, TMAE, tertiary or quaternary amine, or PEI-based resins known in the art (U.S. Pat. No. 6,989,264; Brument et al., Mol. Therapy 6(5):678-686 (2002); Gao et al., Hum. Gene Therapy 11:2079-2091 (2000)). In some embodiments, the anion exchange chromatography media comprises a quaternary amine. In some embodiments, the anion exchange chromatography media is CIM QA (BIA Separations, Slovenia). In some embodiments, the anion exchange chromatography media is BIA CIM® QA-80 (Column volume is 80 mL). One of ordinary skill in the art can appreciate that wash buffers of suitable ionic strength can be identified such that the rAAV remains bound to the resin while impurities, including without limitation impurities which may be introduced by upstream purification steps are stripped away.

In one embodiment, a method of isolating rAAV particles from the clarified feed disclosed herein comprises a first tangential flow filtration, affinity chromatography, anion exchange chromatography, and a second tangential flow filtration. In one embodiment, the isolating the rAAV particles further comprises a sterile filtration.

In one embodiment, the method further comprises determining the vector genome titer of a composition comprising the isolated recombinant rAAV particles comprising measuring the absorbance of the composition at 260 nm; and measuring the absorbance of the composition at 280 nm. In one embodiment, the method further comprises determining the capsid titer of a composition comprising the isolated recombinant rAAV particles comprising measuring the absorbance of the composition at 260 nm; and measuring the absorbance of the composition at 280 nm.

In one embodiment, the rAAV particles are not denatured prior to measuring the absorbance of the composition. In one embodiment, the rAAV particles are denatured prior to measuring the absorbance of the composition.

In one embodiment, the absorbance of the composition at 260 nm and 280 nm is determined using a spectrophotometer.

In one embodiment, the absorbance of the composition at 260 nm and 280 nm is determined using a HPLC. In one embodiment, the absorbance is peak absorbance.

Several methods for measuring the absorbance of a composition at 260 nm and 280 nm are known in the art. Methods of determining vector genome titer and capsid titer of a composition comprising the isolated recombinant rAAV particles are disclosed in the International Application titled "SYSTEMS AND METHODS OF SPECTROPHOTOMETRY FOR THE ESTIMATION OF CONTENT, CAPSID CONTENT AND FULL/EMPTY RATIOS OF ADENO-ASSOCIATED VIRUS PARTICLES," filed on Apr. 29, 2019, which claims the priority of U.S. Provisional Application Nos. 62/664,251 filed on Apr. 29, 2018, 62/671,965 filed on May 15, 2018, and 62/812,898 filed on Mar. 1, 2019, respectively, each of which is incorporated herein by reference in its entirety.

In additional embodiments the disclosure provides compositions comprising isolated recombinant rAAV particles produced by a method disclosed herein. In some embodiment, the composition is a pharmaceutical composition comprising a pharmaceutically acceptable carrier.

As used herein the term "pharmaceutically acceptable" means a biologically acceptable formulation, gaseous, liquid or solid, or mixture thereof, which is suitable for one or more routes of administration, in vivo delivery or contact. A "pharmaceutically acceptable" composition is a material that is not biologically or otherwise undesirable, e.g., the material may be administered to a subject without causing substantial undesirable biological effects. Thus, such a pharmaceutical composition may be used, for example in administering rAAV isolated according to the disclosed methods to a subject. Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions. Pharmaceutical compositions can be formulated to be compatible with a particular route of administration or delivery, as set forth herein or known to one of skill in the art. Thus, pharmaceutical compositions include carriers, diluents, or excipients suitable for administration by various routes. Pharmaceutical compositions and delivery systems appropriate for rAAV particles and methods and uses of the invention are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

In some embodiments, the composition is a pharmaceutical unit dose. A "unit dose" refers to a physically discrete unit suited as a unitary dosage for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dose forms may be within, for example, ampules and vials, which may include a liquid composition, or a composition in a freeze-dried or lyophilized state; a sterile liquid carrier, for example, can be added prior to administration or delivery in vivo. Individual unit dose forms can be included in multi-dose kits or containers. Recombinant vector (e.g., AAV) sequences, plasmids, vector genomes, and recombinant virus particles, and pharmaceutical compositions thereof can be packaged in single or multiple unit dose form for ease of administration and uniformity of dosage. In some embodiments, the composition comprises rAAV particles comprising an AAV capsid protein from an AAV capsid serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise an AAV capsid protein from an AAV capsid serotype selected from AAV-1, AAV-2, AAV-5, AAV-6, AAV-7, AAV-8, AAV-9, AAV-10, AAVrh.8, and AAVrh. 10. In some embodiments, the AAV capsid serotype is AAV-8. In some embodiments, the AAV capsid serotype is AAV-9.

EXAMPLES

Example 1. Schematic Process for the Clarification of a 50 Liter Suspension Culture by Multi-Stage Filtration A suspension culture comprising recombinant AAV particles can be clarified using a filter train as depicted in FIG. 1, comprising Clarisolve® 20 MS (2×0.11 m$^2$), Millistak+® COHC (0.11 m$^2$), and Sartopore® 2 XLG 0.2 µm (0.13 m$^2$) filters. The clarification process can be performed as follows:
 (a) assemble the filter train;
 (b) connect pump inlet to clarification buffer;
 (c) connect the filter train outlet to an appropriately sized waste bag;
 (d) equilibrate the filter train with ≥15 L of clarification buffer at 200 LMH (Clarisolve®, 733 mL/min);
 (e) stop the pump;
 (f) connect the pump inlet to the bioreactor bag outlet;
 (g) set the pump speed to 200 LMH;
 (h) begin to filter the harvest while maintaining filter pressures within pre-specified limits;
 (i) once ~6 liters have been collected into the waste vessel, connect the filtration outlet to the collection bag;
 (j) continue to filter the harvest until the entire contents of the bioreactor have been filtered;
 (k) stop the pump
 (l) connect the pump inlet to clarification buffer;
 (m) set the pump speed to 200 LMH;
 (n) chase the product with 15 L of clarification buffer, continuing to collect into the collection bag;
 (o) disconnect the pump inlet from the clarification buffer;
 (p) continue to pump air through the filters until the floor scale measuring filtrate weight stabilizes;
 (q) stop the pump and disconnect the collection bag from the filtration inlet;
 (r) prior to sampling or processing the filtrate in the collection bag, ensure that the filtrate is sufficiently mixed.

The clarified filtrate is ready for subsequent processing, for example, by tangential flow filtration or chromatography.

Figure 2:
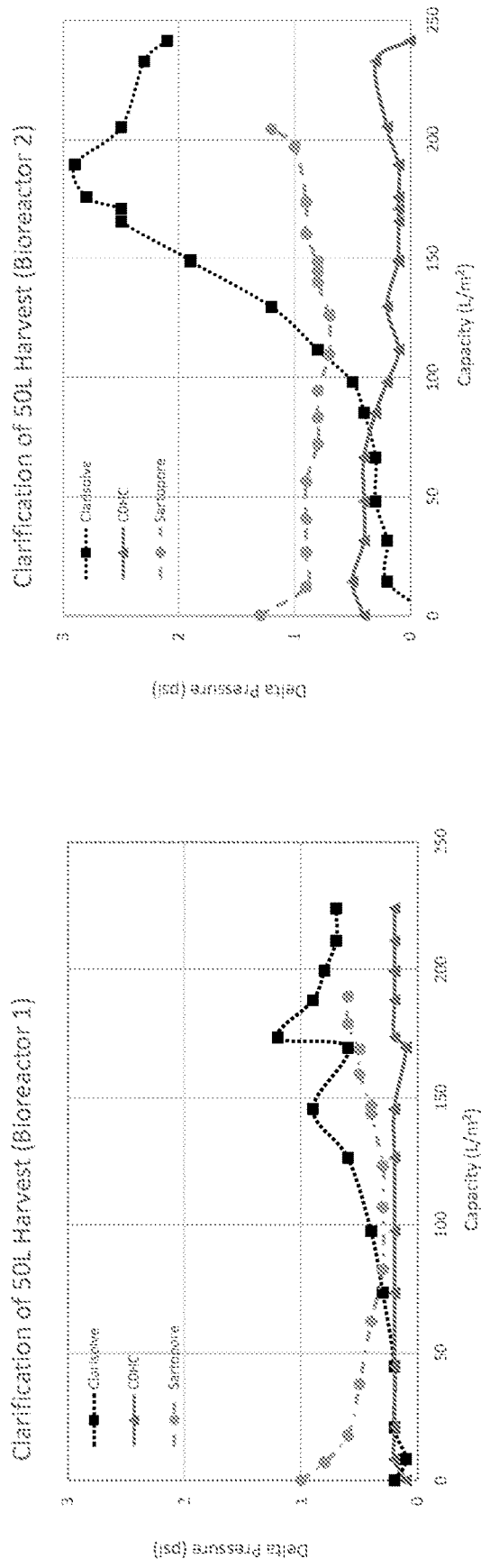
FIG. 2 shows pressure profiles and capacity results for the clarification of two 50 liter suspension cultures produced by different bioreactors using a filter train of Clarisolve® 20 MS, Millistak+® COHC, and Sartopore® 2 XLG 0.2 µm filters.

Example 2. Clarification of Two 50 Liter rAAV8 Suspension Cultures by Multi-Stage Filtration Two ~50 Liter suspension cultures comprising recombinant AAV8 cultures produced in different bioreactors were clarified by multi-stage filtration (FIG. 2). The filter train comprised Clarisolve® 20 MS (2×0.11 m$^2$ providing a total of 0.22 m$^2$), Millistak+® COHC (2×0.11 m$^2$ providing a total of 0.22 m$^2$), and Sartopore® 2 XLG 0.2 µm (0.13 m$^2$) filters. Millipore Pilot Scale Pod Holder was set up according to the manufacturer's user guide with Clarisolve 20 MS and COHC filters placed in the pod holder, separated by a divider plate. Sartopore 0.8/0.2 filter was connected to the COHC outlet. Filters and pressure transducers were connected with Masterflex platinum-cured silicone tubing. Clamp rod knobs were tightened, the hydraulic pump was set to between 62 and 76 bar. To prepare filters for use, they were sequentially purged of air by filling with MilliQ water at a slow 60 LMH flux, rinsed clean of leachables and extractables with 100 L/m$^2$ MilliQ at 600 LMH flux, and equilibrated with one and half filter hold-up volumes of 20 mM Tris, 200 mM NaCl, pH7.5. Pressure on each filter was tracked by a PendoTech pressure monitor. Process data, including changes in pressures, pressure differentials (ΔP), and filtrate weights were recorded every 3-5 minutes. Sample clarification was performed at a flux of 200 LMH. FIG. 2 shows that the filter train clarifies the 50 L harvest samples from Bioreactor 1 and 2 with pressures less than 2 psig and 3 psig, respectively. Turbidity of the initial feed ("Initial Turbidity"), turbidity of the clarified filtrate ("Final Turbidity"), and the yield of the clarification process are shown in Table 1. The clarified filtrate was further processed by a first tangential flow filtration, affinity chromatography, anion exchange chromatography, and a second tangential flow filtration to produce isolated recombinant AAV8 particles.

TABLE 1

Summary of Turbidity Reduction and Genome Copy (GC) recovery of 50 L Scale Runs for rAAV8 and 100 L scale run for rAAV9

| | Initial Turbidity (NTU) | Final Turbidity (NTU) | GC Recovery |
|---|---|---|---|
| rAAV8 - 50 L, Bioreactor 1 | 1,220 | 1.38 | 87.7% |
| rAAV8 - 50 L, Bioreactor 2 | 917 | 2.07 | 96.8% |
| rAAV9 - 100 L | 1,640 | 7.31 | 111.7% |

Figure 3:
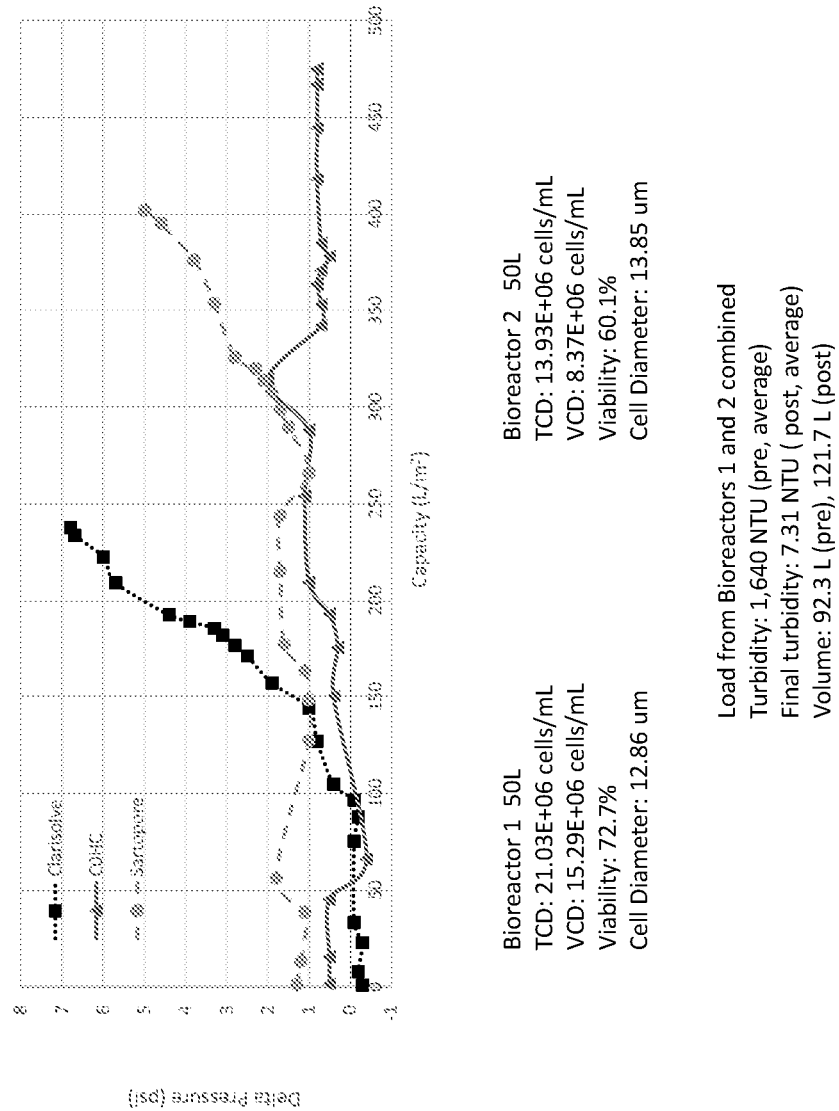
FIG. 3 shows the pressure profile and capacity result for the clarification of a 100 liter suspension culture using a filter train of Clarisolve® 20 MS, Millistak+® COHC, and Sartopore® 2 XLG 0.2 µm filters.

Example 3. Clarification of 100 Liter rAAV9 Suspension Cultures by Multi-Stage Filtration Two ~50 Liter suspension cultures comprising recombinant AAV9 cultures produced in different bioreactors were combined and clarified by multi-stage filtration of similar setting as in Example 3 (FIG. 3). The filter train comprised Clarisolve® 20 MS (1×0.33 m$^2$ and 1×0.11 m$^2$ providing a total of 0.44 m$^2$), Millistak+® COHC (2×0.11 m$^2$ providing a total of 0.22 m$^2$), and Sartopore® 2 XLG 0.2 µm (0.26 m$^2$) filters. The filtration was performed at a flux of 200 LMH. Pressure profile and capacity result reveal that the filter pressure was high on both Clarisolve 20 MS and Sartopore 0.8/0.2, rising to a high of 6.8 and 5 psig respectively, suggesting that larger surface areas for both Clarisolve 20 MS and Sartopore 0.8/0.2 can be used for rAAV9 clarification. Turbidity of the initial feed ("Initial Turbidity"), turbidity of the clarified filtrate ("Final Turbidity"), and the yield of the clarification process are shown in Table 1 above. The clarified filtrate was further processed by a first tangential flow filtration, affinity chromatography, anion exchange chromatography, and a second tangential flow filtration to produce isolated recombinant AAV9 particles.

While the disclosed methods have been described in connection with what is presently considered to be the most practical and preferred embodiments, it is to be understood that the methods encompassed by the disclosure are not to be limited to the disclosed embodiments, but on the contrary, is intended to cover various modifications and equivalent arrangements included within the spirit and scope of the appended claims.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

What is claimed is:

1. A method for the clarification of a feed containing recombinant adeno-associated virus (rAAV) particles and an impurity comprising: (a) providing a feed comprising a suspension cell culture; (b) pretreating the feed by adding salt to a final concentration between about 0.2 M and about 0.6 M; (c) applying the pretreated feed to a filter train comprising a primary depth filter connected to a secondary depth filter, wherein the outflow of the primary depth filter is connected to the inflow of the secondary depth filter; (d) applying a buffer comprising 200 mM salt to the filter train after step (c); and (e) recovering a filtrate comprising the rAAV particles, wherein (i) the impurity comprises cells or cellular debris, (i) the method separates the rAAV particles from the impurity without the use of centrifugation or tangential flow microfiltration prior to (a), (iii) the feed volume is between about 100 liters and about 3000 liters, and (iv) steps (c) and (d) are performed at a flux between about 175 L/m$^2$/hr (LMH) and about 225 LMH.

2. The method of claim 1, wherein the filter train further comprises a tertiary filter connected to the secondary depth filter, wherein the outflow of the secondary depth filter is connected to the inflow of the tertiary filter.

3. The method of claim 1, wherein the primary depth filter comprises a porous depth filter media comprising at least 2 graded layers of non-woven fibers having a total thickness of about 0.3 cm to about 3 cm, and wherein each of the at least 2 graded layers of non-woven fibers have a nominal pore size rating more than about 40 μm.

4. The method of claim 1, wherein the secondary depth filter comprises a media comprising a composite of cellulose and diatomaceous earth.

5. The method of claim 2, wherein the tertiary filter comprises a sterilizing grade filter media.

6. The method of claim 1, wherein the ratio of primary filter area to secondary filter area is between about 1:3 and about 3:1.

7. The method of claim 2, wherein the ratio of primary filter area to tertiary filter area is between about 1:3 and about 3:1.

8. The method of claim 2, wherein the ratio of primary filter area to secondary filter area to tertiary filter area ratio is within the range of about 0.3-3 to about 0.3-3 to about 0.2-5.

9. The method of claim 1, wherein the suspension culture is comprises a culture of Human Embryonic Kidney 293 HEK293 cells.

10. The method of claim 1, wherein the culture has a total cell density of between about $1 \times 10^6$ cells/ml and about $30 \times 10^6$ cells/ml.

11. The method of claim 1, wherein the salt in step (b) is NaCl.

12. The method of claim 1, wherein the rAAV particles comprise an AAV capsid protein from an AAV selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

13. The method of claim 12, wherein the AAV capsid serotype is AAV-8 or AAV-9.

14. The method of claim 1, wherein the feed volume is between about 500 liters and about 3000 liters.

15. A method for producing a composition comprising isolated recombinant adeno-associated virus (rAAV) particles from a feed comprising an impurity, comprising
  (a) clarifying the feed according to the method of claim 1, and
  (b) isolating the rAAV particles from the filtrate by one or more of tangential flow filtration, affinity chromatography, size exclusion chromatography, ion exchange chromatography, and hydrophobic interaction chromatography.

16. The method of claim 15, wherein the isolating the rAAV particles comprises a first tangential flow filtration, affinity chromatography, anion exchange chromatography, and a second tangential flow filtration.

17. The method of claim 1, wherein the feed is not pretreated with a chemical flocculent.

* * * * *